(12) United States Patent
Zhou et al.

(10) Patent No.: US 11,864,833 B2
(45) Date of Patent: Jan. 9, 2024

(54) EYE-IMAGING APPARATUS AND METHOD EMPLOYING SEQUENTIAL FLASHING OF ILLUMINATION LIGHT IN SYNCHRONIZATION WITH THE OPERATION OF AN IMAGE SENSOR

(71) Applicant: Natus Medical Incorporated, Pleasanton, CA (US)

(72) Inventors: Yan Zhou, Pleasanton, CA (US); Willem Crone, Malin, OR (US); John Allison, Pleasanton, CA (US)

(73) Assignee: Natus Medical Incorporated, Middleton, WI (US)

( * ) Notice: Subject to any disclaimer, the term of this patent is extended or adjusted under 35 U.S.C. 154(b) by 527 days.

(21) Appl. No.: 16/948,992

(22) Filed: Oct. 8, 2020

(65) Prior Publication Data
US 2021/0106224 A1   Apr. 15, 2021

Related U.S. Application Data

(60) Provisional application No. 62/913,706, filed on Oct. 10, 2019.

(51) Int. Cl.
*A61B 3/10* (2006.01)
*A61B 3/117* (2006.01)
(Continued)

(52) U.S. Cl.
CPC .............. *A61B 3/14* (2013.01); *A61B 3/0008* (2013.01); *A61B 3/125* (2013.01); *A61B 3/1208* (2013.01); *A61B 3/1241* (2013.01); *G02B 6/0008* (2013.01)

(58) Field of Classification Search
CPC ......... A61B 3/02; A61B 3/102; A61B 3/1025; A61B 3/113; A61B 3/1015; A61B 3/103; A61B 3/117; A61B 3/1225
(Continued)

(56) References Cited

U.S. PATENT DOCUMENTS 4,026,638 A * 5/1977 Govignon .............. A61B 3/125
359/740
4,265,519 A   5/1981 Pomerantzeff
(Continued)

FOREIGN PATENT DOCUMENTS

DE   102006006028 A1 * 8/2007 ........... G09B 21/008
EP       807832 A2   11/1997
(Continued)

OTHER PUBLICATIONS

European Patent Office—Laszlo Horvath, International Search Report, International Application No. PCT/US2020/070638, dated Feb. 24, 2021.

*Primary Examiner* — Dawayne Pinkney
(74) *Attorney, Agent, or Firm* — Daniel C. Pierron; Widerman Malek, PL

(57) ABSTRACT

An eye-imaging apparatus and system is described including circular fiber array ends arranged at skewed angles relative to the optical axis of the imaging path, a light intensity distribution converter along the illumination path to convert a bell-shaped distribution into a top-hat distribution, an image sensor, and high frequency response light source(s) operating in flash illumination mode in synchronization with the image sensor. As a result, unnecessary exposure of illumination light to a patient eye is minimized while the illumination light can span a wide enough coverage range with desired intensity and spectral distribution to cover the desired angular field of view and spectral range on a retina.

12 Claims, 15 Drawing Sheets

(51) Int. Cl.
  *A61B 3/12*   (2006.01)
  *G02C 7/04*   (2006.01)
  *A61B 3/14*   (2006.01)
  *A61B 3/00*   (2006.01)
  *A61B 3/125*  (2006.01)
  *F21V 8/00*   (2006.01)

(58) Field of Classification Search
  USPC ........ 351/200, 205, 206, 209–211, 219, 221, 351/246, 159.02
  See application file for complete search history.

(56) References Cited

U.S. PATENT DOCUMENTS

| | | | |
|---|---|---|---|
| 11,154,193 B2* | 10/2021 | Toslak | A61B 3/0008 |
| 11,457,146 B1* | 9/2022 | Ng | H04N 23/60 |
| 2014/0078467 A1 | 3/2014 | Su | |

FOREIGN PATENT DOCUMENTS

| | | | |
|---|---|---|---|
| JP | 2017212026 A | 11/2017 | |
| WO | 2015054797 A1 | 4/2015 | |

\* cited by examiner

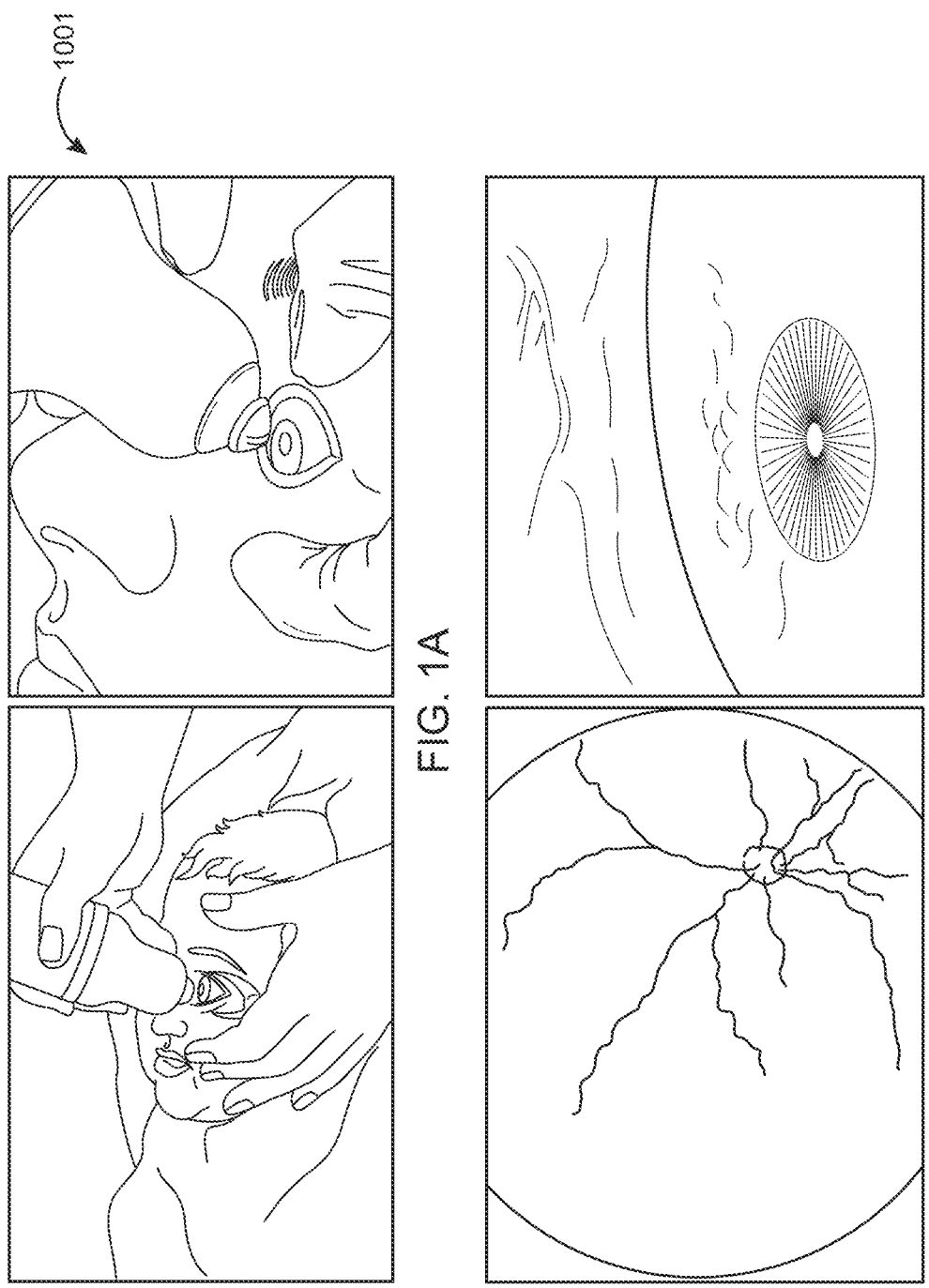

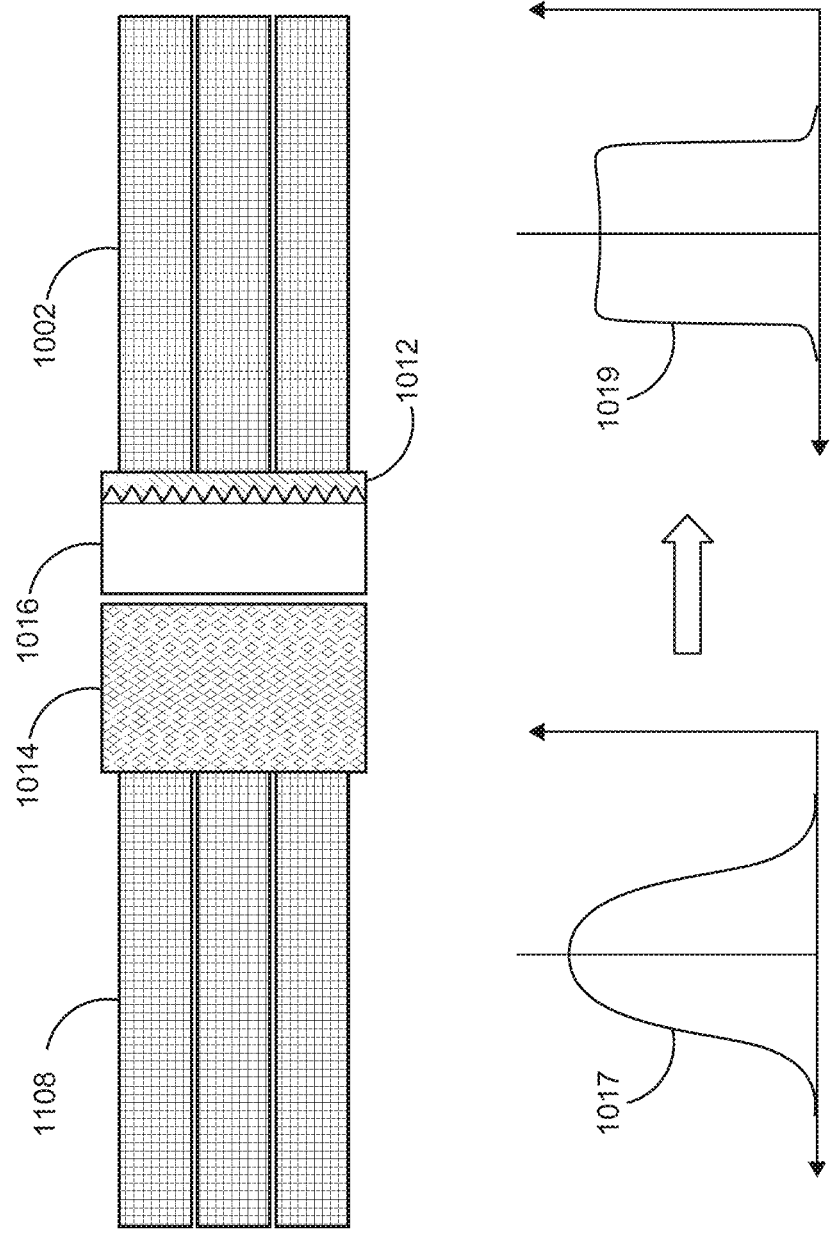

EYE-IMAGING APPARATUS AND METHOD EMPLOYING SEQUENTIAL FLASHING OF ILLUMINATION LIGHT IN SYNCHRONIZATION WITH THE OPERATION OF AN IMAGE SENSOR

RELATED APPLICATION DATA

This application claims priority to U.S. Provisional Patent Application 62/913,706 titled Eye-imaging System and Device with Improved Illumination Performance and filed Oct. 10, 2019, the details of which are incorporated herein in their entireties except to the extent disclosure therein is inconsistent with disclosure herein.

TECHNICAL FIELD OF THE INVENTION

An eye imaging system and apparatus which uses an imaging sensor for imaging and a high frequency response light source for illumination, with sequential flashing of the light source(s) in synchronization with the global shutter of an imaging sensor to improve illumination usage efficiency.

BACKGROUND

The present invention relates to ophthalmoscopes, operation microscopes and other instruments for viewing and imaging the interior of the human eye. More particularly, the invention provides an illumination apparatus and system including synchronization means with a global shutter image sensor, serving to provide improved illumination usage efficiency and illumination uniformity over a large angular field of view for diagnostic and documentation purposes of the human eye. The invention also provides the possibility of avoiding hazy or low contrast images, bright and/or dark illumination spots, the need of large pupil dilation, and color channel crossing talking.

Cameras for imaging the eye must meet several technical objectives. It is preferable, and for some clinical diagnoses required, to obtain color images of the eye. Also, in some instances such as fluorescein angiography, blue excitation induced fluorescence images are required. For some applications, an eye imaging camera should offer the option of providing very high spatial resolution for diagnosis of certain ocular diseases. For example, when examining the neural fiber layer, high resolution is required.

Moreover, wide field-of-view (FOV) images of the eye are necessary for evaluating some pathologies of the eye. Exemplar pathologies include, but are not limited to, retinopathy of prematurity (ROP) where the demarcation line between avascular retina and vascularized retina occurs often on the peripheral region of the retina, and ocular tumors which, in many cases, lie on or spread to the periphery of the retina. When examining only the optical disk, a 30 degree wide FOV is sufficient. For studies of ROP and tumors located on the periphery of the retina and other optical disorders, a FOV of 120 degrees and even larger is preferred. The intensity of light required for imaging is also a consideration as light safety requirements need to be met. Scattering and reflection of the illumination light from ocular structures other than the retina can also substantially reduce the contrast of the image. Imaging using electronic array sensors such as Complementary Metal Oxide Semiconductor (CMOS) and charged coupled devices (CCD) instead of film is highly desired as well. Electronic sensor array-based cameras tend to be more sensitive than film, reducing the amount of illumination light required, thus reducing potential hazard to a patient eye. Electronic sensors and displays also allow instant and live view/review of the image, in addition to possibly providing various image processing operations without a noticeable time delay. One issue generally associated with electronic image sensors is that its electronic shutter that opens to receive light can be different for different pixels and also there are times when the shutter is turned off while the illumination light is still on. In the case of eye fundus or retina imaging, this can result in a unnecessary exposure of a patent eye to the illumination light as not all the illumination light are fully utilized to produce signal on the image sensor, which is a non-ideal case in terms light safety for a patient eye being imaged.

As described in the art, in order to image the eye, a system must optically relay the spherical concave retina onto a flat image sensor (2D) plane. Further to the above, in conventional systems background haze is created when the light used to illuminate the retina is reflected and/or scattered by the cornea and ocular lens with such returned illumination light being channeled to the image sensor. The reflections from the optical interfaces of the cornea and ocular lens are also known as Purkinje images. A "first Purkinje image" is the reflection from the outer surface of the cornea, the second is the reflection from the inner surface of the cornea, the third is the reflection from the outer surface of the ocular lens, and the fourth emanates from the inner surface of the ocular lens. As described in the art, the first Purkinje image may be mostly avoided with careful control of positioning of an imaging device near the patient's eye and with the use of optical coupling gel between the device and the cornea. Further, subsequent Purkinje images need to be removed in the post process phase and/or minimized from appearing on the image in the first place.

Systems have been developed to minimize the effect of Purkinje images during ophthalmic visualization. In one such system, the light emitted from the lenspiece of an ophthalmoscope is conditioned by a relatively large inner diameter optical fiber annular array ends through a microstructured light guide or diffuser. However, this creates a side effect of reducing the amount of light transmitted and creating scattered light, which can negatively impact certain eye examinations, such as those for retinopathy of prematurity (ROP) in premature infants, which require a wide field of view. In addition, the larger diameter of the optical fiber array and the corresponding micro-structured light guide or diffuser imposes the need for a larger pupil size.

Eye-imaging systems and devices known in the art include handheld eye imaging devices that are especially suitable for imaging the eye of non-cooperative patients like newborns and infants. These systems use either (1) a three-chip camera with bulk RGB (or Red, Green and Blue) color splitter(s) to channel different color bands to different sensor chips, or (2) a one-chip color camera with patterned color filter array on top of the image sensor, or (3) a monochrome one-chip camera in combination with synchronized sequentially flashed illumination of different colors (R, G, and B). In the third or last case, a pseudo full color image cam be produced after the individual color images are registered and digitally combined, (examples include US 20060268231 and U.S. Pat. No. 3,954,329). An issue associated with the three-chip image sensor/camera is its much higher price as compared to a one-chip image sensor. An issue associated with a one chip color image sensor/camera is its color mixing or low color fidelity and also the non-full utilization of the illumination light as some of the patterned filters will reject certain illumination color band(s). An issue associated with a monochrome image sensor/camera in combination with synchronized sequential illumination color flashing is that the color fidelity will degrade if non-controlled illumination light, such as illumination from day light or from room lighting also illuminate the patient eye when an external eye image is captured.

In addition, prior art related to illuminating a large angular field of view for uniform illuminator imaging includes the use of various micro-structured light conditioning optical elements arranged in between the front most optical element (the contact lens) of the imaging device and a circular array of optical fibers or free space optical designs to redistribute the illumination light before light enters an eye. Currently, most of the uniform illuminator viewing and imaging systems illuminate the interior of the eye through the pupil of the eye by a light source that is channeled to land as a ring around the imaging path near the cornea and is directed into the posterior segment of the eye.

Moreover, when used to obtain color images of the retina, these systems apply light sources that produce light containing blue (B), green (G), and red (R) wavelengths. Because the retina is illuminated through the pupil of the eye, these systems can suffer from light illumination reflections off the cornea, ocular lens, and its interface with the vitreous cavity. They need typically more than half of the pupil area for illumination, and when attempting to view portions of the interior of the eye more peripheral than the macula, the effective pupil size that is available becomes smaller and light is not transmitted through fully. As a result, standard uniform illuminator viewing and imaging systems depend strongly on clear ocular media and on wide pupil dilation and they are generally limited to a maximum of 60° field of view and cannot observe the periphery much beyond the posterior pole.

To avoid the unwanted illumination light reflections from landing on the image sensor, the illumination ring at the cornea and ocular lens region is generally arranged to land outside the imaging path. Polarization means has also been used to reduce these illumination light reflections. Examples of such systems include U.S. Pat. Nos. 5,822,036, 8,836, 778, 9,351,639, 9,872,618 and 10,258,232. A common issue associated with these designs is that the illumination on the retina has limited uniformity or limited field of view. In general, on the image sensor plane, a donut shaped illumination distribution is detected, leading to darker illumination at the peripheral and central regions than at mid field of view regions.

The problems associated with illuminating the interior of the eye through the pupil can be avoided when the interior of the eye is illuminated through the sclera (synchronized sequential color illumination), as first proposed by Pomerantzeff in U.S. Pat. No. 3,954,329. This system supports the use of a low cost monochrome image sensor and wide angle uniform illuminator imaging without demanding pupil dilation and while bypassing illumination difficulties that may rise due to obstruction and scattering from opacities in the anterior eye chamber and any other intervening ocular structures. Relatedly a system (Panoret-1000™ of Medibell Medical Vision Technologies, Ltd.) that is based on U.S. Pat. No. 5,966,196 (Svetliza, et al.) and U.S. Pat. No. 6,309,070 (Svetliza, et al.) has applied synchronized sequential color illumination according to the method disclosed in the '329 patent referenced above.

However, illuminating through the sclera requires much higher optical power or energy than illuminating through the pupil and there exists a possibility that the unsafe strong illumination light is transmitted through the pupil. This can happen when live imaging is ongoing while a handheld image capture unit is moved around relative to a patient eye while a live video display of the retina image is being monitored. In addition, blue light, which is much more hazardous to a patient eye, can be substantially more absorbed than red and green light by the sclera. As a result, more blue illumination light is needed, which is an even less safe circumstance for the patient.

Given the above-mentioned limitations and/or issues, there exists a need for improvement in illumination uniformity for wide angular field of view optical imaging systems. There also exists a need to reduce the system cost associated with a three-chip color image sensor/camera while achieving similar color fidelity as can be provided by such a camera. There is especially a need for improvement in illumination usage efficiency to reduce and minimize unnecessary exposure of illumination light to a patient eye from the point of light safety consideration.

Accordingly, it is a first object of this invention to provide an eye-imaging apparatus and a system for obtaining images of the interior of the eye with improved illumination uniformity and substantially reduced background light noise. The uniformly illuminating eye-imaging apparatus and system described herein includes various light distribution conditioning means in addition to unique spectral illumination filters. In use, light is disposed along an illumination light path, ultimately forming uniformly illuminated images of a given eye locus on an image sensor plane. The uniformly illuminating eye-imaging apparatus and system employ synchronized sequential illumination in addition to other features resulting in redistribution of light.

It is another objective of the invention to employ a large numerical aperture (NA) optical fiber to output light with a large illuminating cone angle. Yet another embodiment employs a light re-distribution element at one or more locations along the illumination optical fiber such that the light output from the fiber end is converted from having a bell-shape intensity distribution to one having a hat-top intensity distribution. Still another approach directs the illumination light from each coordinated illuminator fiber end (i.e., an illumination optical fiber end) at a skewed angle to enter the eye such that illumination light reflections from the cornea and ocular lens optical interfaces are mostly directly away from the imaging path. As a result, the inner diameter of the annular fiber array ends can be smaller than that of the prior art, thus reducing the need for a relatively large pupil size. Each of the embodiments can be implemented independently or combined with other approach(es) known in the art. Further to the above, the present invention relies on various light distribution elements and uniquely-arranged aperture fibers.

The illuminator fibers may include a high numerical aperture and further include circular fiber array ends arranged at a skewed angle relative to the optical axis of the imaging path. Said skewed angle relative to the optical axis of the imaging path may be at least 30 degrees, 35 degrees, 40 degrees, or the like. Said light redistribution element may be a micro-prism array disposed along the optical fiber illumination light path. Said illuminator fibers (also referred to herein as "fibers" or "plastic fibers") are of at least 0.60 NA (Numerical Aperture) and include an illumination variation of less than or equal to at least twenty five percent variation in the preferred embodiment.

It is another objective of the invention to employ a single chip high frame rate global shutter image sensor with a color filter array (such as a Bayer pattern RGB color filter array) in combination with sequentially flashed illumination light of different colors (such as R, G, & B or W) to construct a handheld eye imaging device. An embodiment employs the synchronization of the flashing of the different color light source(s) with the electronic shutter opening of the image sensor and the use of software to do image data processing to digitally register and combine images filtered by the color filter array of the image sensor that are associated with the substantially flashed illumination light. As a result, illumination usage efficiency and color fidelity or purity can be improved, while the cost of the camera is kept low and the color image is not substantially degraded as compared to the pure pseudo sequential color scheme when the overall illumination on an object is dominated by surrounding background lighting such as that from room lighting sources rather than from the illumination source of the device.

The invention also involves the recognition that there can be advantages to high frequency pulse width modulation to control the averaged amount of illumination light on the retina while the flashing of the illumination light is synchronized sequentially with each of the red, green, and blue or white wavelengths on a one-chip color image sensor for obtaining improved illumination usage efficiency and also possibly a high visual wavelength fidelity optical RGB image. In this case, the control of the illumination light output is done with pulse width modulation so the spectral peak position shift is minimized and at the same time, unnecessary exposure of illumination light to a patient eye is reduced and minimized, which can help in meeting light safety requirements with improved margins in comparison to the continuous illumination case. Such high frequency response light source can be flashed in synchronization with and at the image sensor frame rate and within each flash the light source is pulsed at high repetition rates (at least 10 times and preferably more than 100 times the frame rate of the image sensor) with a certain desired duty cycle and peak value to enable multiple pulses of the illumination light landing on the image sensor only when the global shutter is on and also to use pulse width modulation (PWM) to control averaged amount of light output within each flash. According to the invention, such technologies could be used for the acquisition of color images of the retina while providing desired wavelength or wavelengths.

In one embodiment, at least one of the duty cycle of the red, or green or blue light sources is controlled such that the effective optical energy or effective number of photons in each of the red, green and blue color channels from the image sensor is better balanced so the electronic gain (analog and/or digital) of each of the red, green and blue channels are approximately the same per the white balancing need. In other words, auto-white balancing is primarily achieved through the control of the ratio of the duty cycles of the red, green and blue light sources per the PWM modulation scheme. This ratio can be maintained relatively the same while the overall duty cycle is increased or decreased when the averaged amount of light output is changed to ensure that the electronic gain of the image sensor for the red and blue relative to that of the green is maintained close to each other per the white balancing need, which will avoid un-necessarily higher electronic noise in one or more of the image sensor color channels.

In another embodiment, the PWM pulse peak value within each flash is controlled achieve auto-white balancing among the red, green and blue channels such that as long as the LED dies can handle a certain PWM pulse peak within light safety limit, the effective optical energy or effective number of photons in each of the red, green and blue color channels from the image sensor can be better white balanced so the electronic gain of each of the red, green and blue channels are approximately the same per the white balancing need. In other words, the PWM pulse peak values of the red, green and blue flashes have a constant relative ratio as needed for white balancing such that auto-white balancing is primarily achieved through the control of the ratio of the duty cycles of the red, green and blue light sources per the PWM modulation 'scheme. This ratio can be maintained relatively the same while the overall light output is increased or decreased to ensure that the electronic gain of the image sensor for the red and blue relative to that of the green is maintained close to each other per the white balancing need.

In still another embodiment, both the PWM duty cycle and pulse peak value are simultaneously controlled in various possible combinations to achieve the same goal of white balancing. For example, before the PWM duty cycle of any color light approaches 100% when the averaged light output is increased, the duty cycle control scheme can be used. Once the PWM duty cycle of any color light reaches 100%, the PWM pulse peak value of that color light can then be increased to make the averaged, now increased, amount of light of the red, green and blue colors have the desired white balancing needed ratios.

The invention broadly comprises eye imaging apparatus, methods, and systems. Said invention relies on a single chip or a three-chip image sensor operating in synchronization with illumination light source(s), various light distribution elements, and uniquely-arranged aperture fibers. In some embodiments, the methods herein involve illuminating a location within the eye and forming images of an eye locus provided by activation of distinct visual wavelengths. Said images may be formed sequentially and in a synchronous fashion, producing a digitally combined image by digitally stacking the sequential images into a full color image. In some embodiments, said method further comprises engagement with different visual wavelengths including red, green and blue light. In some embodiments, the digitally stacked image is an ultra-high resolution color image. Further, said step of illuminating may be performed by supplying a multi-wavelength illumination source.

The herein described apparatus includes a uniform eye illumination apparatus comprising an illumination filter for propagating desired spectral components of light. A processing assembly for mixing images of different wavelength produce a color image. Further, said processor controls the global shutter image sensor for each image obtained by said eye imaging device. The herein described assembly comprises spectral enhancement illumination filters such as a triband filter and, in some embodiments, an electronically-controlled means of pulse width modulation in combination with image sensor frame rate flashing in order to fully utilize the amount of light directed onto the eye and to balance the signals in the red, green and blue channels of the image sensor.

Further, the invention may comprise an imaging device comprising one or more lenspiece(s) that can be mechanically connected to a common handpiece, and the handpiece may include a visual wavelength image sensor, a color splitting prism or an optical path length compensation glass block, a deep red and/or near infrared cut filter, and an axially movable lens combination for focusing and relaying a real image. Finally, the illuminator fibers may be shielded by a light blocking tube on the outside of the cladding or coated in black paint on the outside of the cladding and may be perpendicularly cleaved at the illuminator fiber tips in some embodiments.

BRIEF DESCRIPTION OF THE DRAWINGS

In order to enhance and improve understanding of the various elements and embodiments of the invention, elements in the figures have not necessarily been drawn to scale. Furthermore, elements that are known to be common and well-understood to those in the industry are not depicted in order to provide a clear view of the various embodiments of the invention. Thus, the drawings are generalized in form in the interest of clarity and conciseness.

FIG. 1A depicts an imaging head of a handheld uniform illumination eye imaging device being positioned close to the eye of a patient with the light coupling medium adherent to the imaging lenspiece for imaging respectively the retina and the anterior chamber of the eye according to one embodiment of the present invention.

FIG. 1B depicts respectively a retina image and an anterior chamber angle image of a patient eye according to one embodiment of the present invention.

FIG. 2C shows some of the illumination path optical elements from the handpiece side to the lenspiece side, in addition to the illumination light intensity distribution change from the handpiece side to the lenspiece side according to one embodiment of the present invention.

DETAILED DESCRIPTION

Figure 2A:
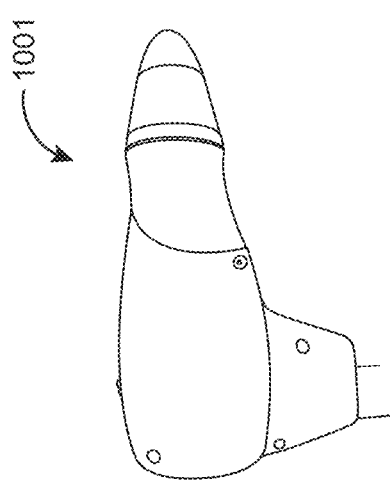
FIG. 2A depicts a wide angular field of view uniform illumination lenspiece attached to a handpiece according to one embodiment of the present invention.

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized, and changes may be made without departing from the scope of the present invention.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term "about" means +/−5% of the recited parameter. All embodiments of any aspect of the invention can be used in combination, unless the context clearly dictates otherwise.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to". Words using the singular or plural number also include the plural and singular number, respectively. Additionally, the words "herein", "wherein", "whereas", "above", and "below" and the like shall refer to this application as a whole and not to any particular parts of the application. Notably "light" is variously referred to herein as "illumination", "illumination beam", "visual wavelength", "color", and the like.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

FIG. 1A illustrates the case when an imaging head of a conventional contact type eye imaging device is being positioned close to the eye of a patient. A light coupling medium may be used to bridge the gap between the end of the imaging lenspiece and the cornea of the patient eye. The left diagram shows how the lenspiece is held for imaging the retina and the right diagram shows how the lenspiece is held for imaging the anterior chamber. Relatedly, FIG. 1B depicts respectively the sketch of a wide-angle retina image (left) and the sketch of an anterior chamber image (right). The present invention is an improvement in that it can enable the capture of a retinal image with a wide angular field of view (up to 130 degrees in some embodiments) with improved illumination uniformity and usage efficiency, and color fidelity. To achieve this, as one of the requirements, there is a need for an optical coupling medium to bridge the gap between the front most optical element and the cornea of a patient eye. When the light coupling medium makes contact with the cornea of the patient eye and the volume of the light coupling medium fills the space between the device and the eye, the light coupling medium will bridge the gap and optically enhance light transmission. This also helps to eliminate a significant amount of optical aberrations originating from the cornea of the eye. FIG. 1A further shows that light coupling medium permits imaging light to easily transmit through the gap, thereby facilitating ophthalmological examination.

Figure 2B:
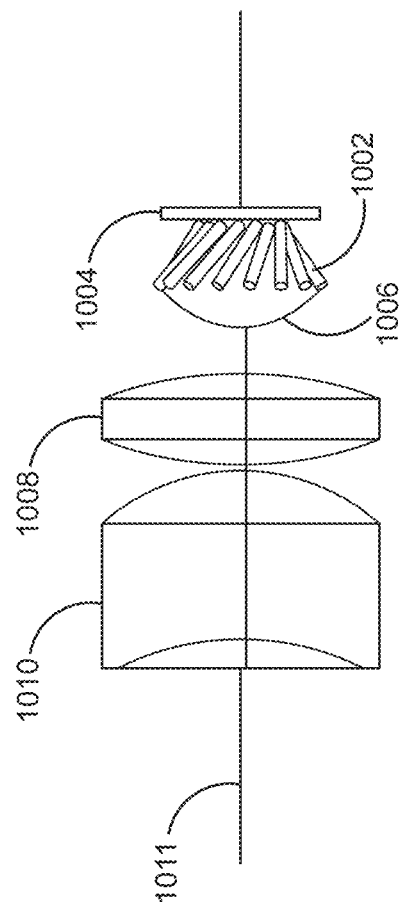
FIG. 2B depicts illumination path and imaging path optical elements of a lenspiece according to one embodiment of the present invention.

FIG. 2A shows an embodiment of the presently invented eye-imaging apparatus 1001 including a handpiece and a lenspiece connected to each other. FIG. 2B shows the imaging path optical elements (1004, 1006, 1008 and 1010) of a lenspiece and a front part of the illumination path optical elements (an array of optical fibers 1002 positioned next to a contact lens 1004 with the fibers skewed at an angle relative to the image path optical axis 1011) of the lenspiece. Illuminator fibers 1002 generally comprise light-transmitting fibers. In some embodiments, plastic multimode optical fibers like the Toray RAYTELA Polymer Optical Fiber PQE-FB 750 are used that have a diameter of 0.75 mm and an NA (numerical aperture) of 0.64. While plastic fibers are mentioned, optic fibers of any type are contemplated and included within the scope of the invention, including glass fibers. The skewed circularly arrayed fibers 1002 are arranged next to each other at the front of the conic lens 1006. The maximum number of fibers of the array 1002 that can be arranged next to each other at the front of the conic lens 1006 is dependent on the fiber diameter, the half cone angle and the front diameter of the conic lens 1006, and the skew angle of the fibers relative to the optical axis 1011. In one embodiment, the front diameter of the conic lens 1106 is about 3.5 mm, the half cone angle of the conic lens 1006 is about 30 degrees, the skew angle of the fibers 1002 relative to the optical axis 1011 is about 40 degrees, and 16 fibers are arranged at the front of the conic lens 1006 next to the contact lens 1004. Such a design will ensure that Purkinje reflections of the illumination light are substantially directed away from entering the imaging path. At the same time, the illumination ring at the iris plane can be relatively small (less than 4.5 mm in the outer diameter of the annular illumination ring there) so the required minimum pupil dilation size for good illumination is about 4.5 mm only.

FIG. 2C shows a micro prism array film based light intensity profile redistribution element (referred to hereafter as, "MPAR") 1012 that is disposed between the light-transmitting fibers 1108 and light-receiving fibers 1002 at the intersection of the handpiece and the lenspiece. In one embodiment, MPAR 1012 is arranged on the lenspiece side (the right side), optically in connection with the transmitting fibers 1108 on the handpiece side. The arrangement enables illumination light to be initially guided through the transmitting fibers 1108, angularly redistributed as light passes through the MPAR 1012, and then received at a receiving end by the receiving fibers 1002. As a result, when light emits from an emitting end at the other side of the receiving fibers 1002, the light intensity angular distribution is changed relative to that from the transmitting fibers 1108.

In some embodiments, the present invention contemplates optic fiber with a large Numerical Aperture (NA), numerical aperture being the characterization of the range of angles over which the optic fiber receives and emits light. For example, receiving fibers 1002 and transmitting fibers 1108 may be fibers with numerical aperture of at least 0.60 NA. In some embodiments, the receiving and transmitting fibers 1002, 1108 may have numerical apertures of 0.64 NA. In one embodiment, the illumination light path initially has a total of 30 plastic fibers that receive light from a light source like an LED light box. These fibers can be in the form of a light guide cable to transmit light to the handpiece, and inside the handpiece it is then split into two sub-cables, each with 15 fibers. At the optical interconnect from the handpiece to the lenspiece, each 15-fiber-port from the handpiece is connected to an 8-fiber-port in the lenspiece and as a result, mechanical connection tolerance is built into the design to ensure relatively consistent light transmission and/or coupling efficiency from the handpiece to the lenspiece.

Further to the above, in one embodiment, the fibers in the lenspiece, especially the portion near the tip of the lenspiece, may have absorptive material positioned on the sides thereof, with the fiber ends being free of absorptive material by perpendicularly cutting or cleaving or lapping/polishing the fiber ends. This ensures that no light escapes from the sides of the fibers to create background optical noise in the captured image. In some embodiments, a black paint may be applied to the sides of the end portion of the fibers. Alternatively, the use of black or light absorbing tubing to encompass the front section of the lenspiece optical fibers can provide the same function as the black paint coating. Doing so will substantially suppress scattered illumination light at the fiber end sections from being channeled to the imaging path, therefore preventing haze or glow at the periphery in the final fundus or retina image. This approach also improves the manufacturability of the lenspiece.

In some embodiments a portrait lenspiece is provided (i.e., a separable lenspiece) for taking an external image of the patient's eye or face. When taking a picture of the patient's face there is no need for the spherical field curvature corrections as in the case of optically relaying a concave spherical retina to a flat image sensor. In such a case, the MPAR may or may not be needed on the portrait lenspiece side as illumination uniformity requirement for external patient eye or face imaging is not as critical as in the case of retina or fundus imaging.

In general, light coupled into a multimode optical fiber and then emitted from the fiber will have a bell-shaped angular optical power or intensity distribution 1017, with more power or intensity distributed around the central angular range of the light emitting cone (i.e. contained among the lower order modes). To convert a bell-shaped angular distribution to a more hat-top or square shaped angular distribution 1019, the thin prism array film (MPAR) 1012 in between the illumination light path of the handpiece and the lenspiece serve the transfer function. As shown in FIG. 2C, the angular light distribution shape changes from that of a bell shape 1017 when light emits from the handpiece fibers to that of a hat-top shape 1019 when light emits from the lenspiece fibers. As a result, the illumination light from a skewed circular array of fibers when landing on the retina can span a wide enough range with substantially improved illumination uniformity. When compared to the prior art, the optical energy will spread more to the peripheral and the center of the retina while also more uniformly covering the desired angular field of view.

Figure 6:
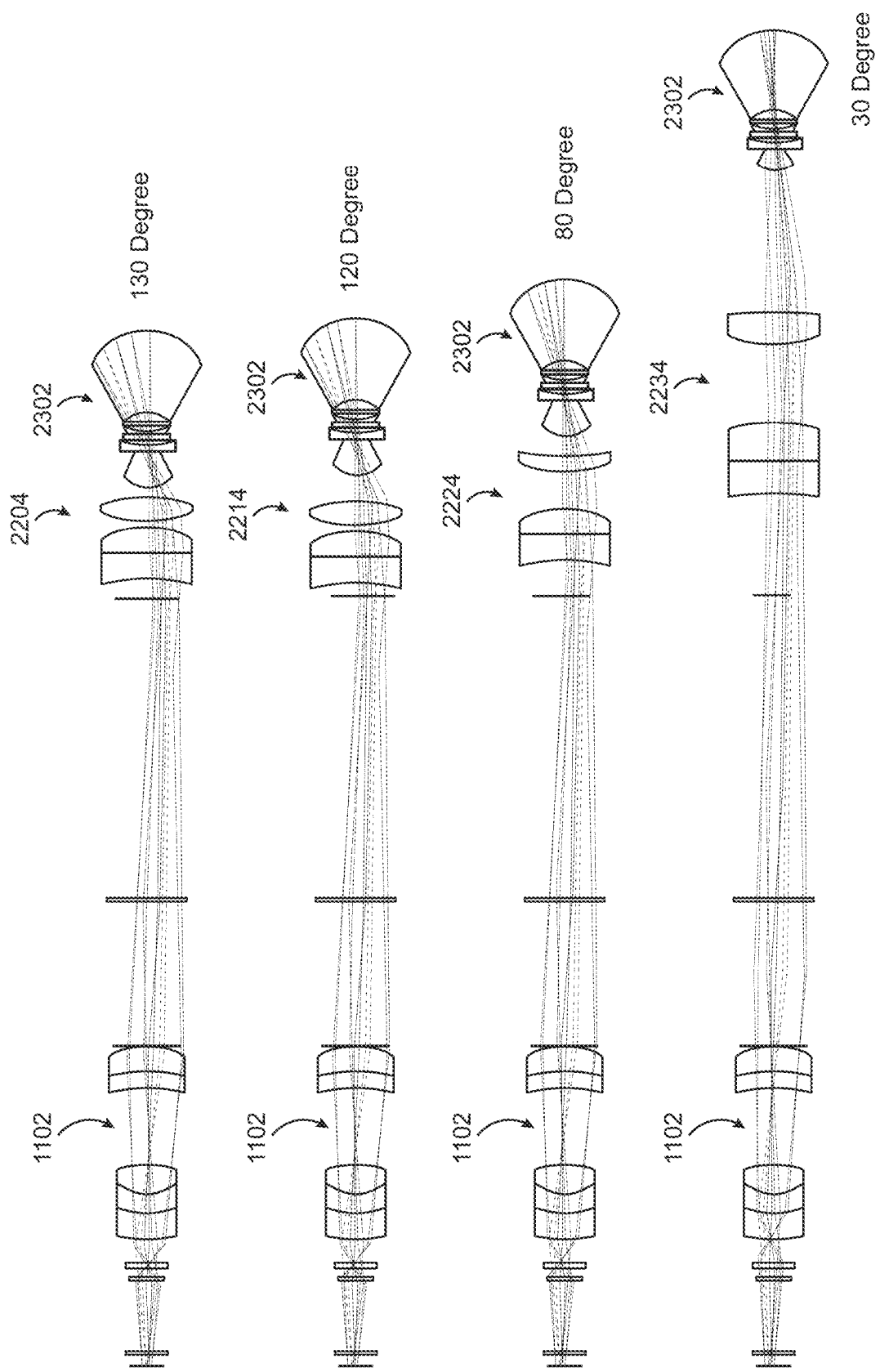
FIG. 6 depicts an imaging path optical design of an eye model with imaging optical elements inside both the handpiece and various lenspieces.

Returning to FIG. 2A, a wide angular field of view retina or fundus imaging lenspiece is shown attached to a handpiece according to one embodiment of the present invention. Notably, the device can be held next to the cornea of a patient eye and with light coupling gel, a wide angular field of view fundus image may be captured. In some embodiments, different lenspieces that are designed to image eye structures such as the retina or fundus with different angular field of views (when each of them is attached to the handpiece) may be used. FIG. 6 shows the optical designs of different lenspieces with different angular FOVs (field of views), i.e. 2204 for 130 degree FOV, 2214 for 120 degree FOV, 2224 for 80 degree FOV and 2234 for 30 degree FOV, being connected to the same handpiece 1102 to form different angular field of view retina or fundus images of the same infant eye 2302.

FIG. 2B shows the optical elements at the front portion of a wide angular field of view lenspiece. Some embodiments of the present invention are such that the angle at which the light emanates from the tip of any given fiber along a light output pointing line of the fiber (being a central line of the light-emitting cone of the fiber) functions to minimize Purkinje reflections being channeled back to the imaging path. As an embodiment of the present invention, the array of illuminator fibers 1002 that terminate next to the front optical element (the contact lens) 1004 are arranged in a skewed manner. In other words, the circular fiber array ends at a skew angle relative to the lenspiece imaging path optical axis 1011 so the fibers are not on a meridional plane of the optical axis 1011 of the imaging path optical lenses, i.e. at a skewed angle relative to the optical axis 1011. Concordantly, the illuminator fibers 1002 may also be arranged such that the light output pointing lines thereof are at a skewed angle relative to each other. The imaging path optical lenses may comprise a contact lens 1004, a conic lens 1006, a mid-position singlet 1008, and a back-position doublet 1010. The contact lens 1004 may be positioned optically proximal of and in contact with the conic lens 1006, the conic lens 1006 is positioned optically proximal of the singlet 1008, and the singlet 1008 is positioned optically proximal of the doublet 1010. In some embodiments, the skew angle relative to the optical axis 1011 may be at least 30 degrees, at least 35 degrees, or at least 40 degrees. Importantly, none are on or across the meridional plane of the optical axis 1011 in said embodiments. Notably, the gap between the contact lens 1004 and the nosepiece (the front endcap housing, not shown in the Figure) of the lenspiece may be sealed in the preferred embodiment, preventing liquid ingress to the lenspiece from its front end. With this skewed fiber angle arrangement, when the illumination light rays hit the front and back surfaces of the cornea and the ocular lens, most of the illumination light rays will be specularly reflected by these surfaces to not enter the imaging path and as a result will not land on the image sensor to produce background optical noise. In other words, when the illumination light beams hit the four Purkinje surfaces, the specularly reflected light rays are mostly directed away from the imaging path. As such, Purkinje images are mostly directed away and minimally captured by the image sensor.

FIG. 2C shows the illumination path optical elements at the interconnect portion between the lenspiece and the handpiece. As an embodiment of the present invention, along the illumination path at the intersection, a micro prism array film based light intensity profile redistribution element 1012 in the form of a micro-prism array film (MPAR) is disposed between the illumination light receiving fibers 1002 on the lenspiece side and the transmitting fibers 1108 on the handpiece side, optically coupling the fibers to bridge them together. In some embodiments, plastic optical fibers with high numerical apertures (for example, NA=0.64) are used. An optical window 1016 is provided on the lenspiece side to protect the MPAR 1012 and the fibers 1002. In some embodiments, a glass rod based optical homogenizer 1014 is used on the handpiece side to both homogenize the illumination light and to protect the illumination optical fibers 1108 in the handpiece. Because there are multiple optic fibers in each fiber cable or sub-cable that can cause light intensity hot spots, by sending all the illumination light through a specialized glass rod homogenizer, said light can thus achieve enhanced uniformity in spatial light intensity distribution. For example, a rod may be within a range of 3-4 mm wide or in diameter and 10 mm long. An optical window 1016 is optically glued to the MPAR 1012 to protect the MPAR 1012 and the optical fibers 1002 in the lenspiece. In general, light coupled into a multimode optical fiber and then emitted from the fiber will have a bell-shaped angular optical power distribution, with more power distributed around the central angular region of the light emitting cone (i.e. contained among the lower order modes). To convert a bell-shaped distribution 1017 to a more hat-top or square-shaped distribution 1019, the MPAR 1012 is used in between the handpiece and the lenspiece. The angular light distribution shape changes from that of a bell shape 1017 when light emits from the handpiece fibers 1108 to that of a hat-top shape 1019 when light emits from the lenspiece fibers 1002 after the transmission of the illumination light from the handpiece side to the lenspiece side. As a result, the illumination light from the skewed circular array of fibers 1002 (as shown in FIG. 2B) when landing on the retina can span a wide enough range with optical energy spreading more to the peripheral and the center of the retina than the bell shape distribution to more uniformly cover the desired angular field of view.

In some embodiments, in order to spread the light more evenly across the retina, a film is used containing a prism material. The film is adhered with glue or the like on either the optical window 1016 side or the optical fiber side or on both sides, and the glue has an index of refraction of the right choice that further helps to spread the light with the desired angular spreading range. The MPAR 1012 may be the 3M™ BRIGHTNESS ENHANCEMENT FILM BEF4 GT 90/24 with a refractive index of 1.66, and the glue on the prism array side may be transparent with a refractive index of 1.348. As a result, when an illumination light ray hits the glue and the prism array interface, it is guided sideways, spreading out with an additional deflection angle. In some embodiments, as shown in FIG. 2C, the prism array 1012 induces the distribution of light to transform from a bell curve to more square-like curve.

Figure 3:
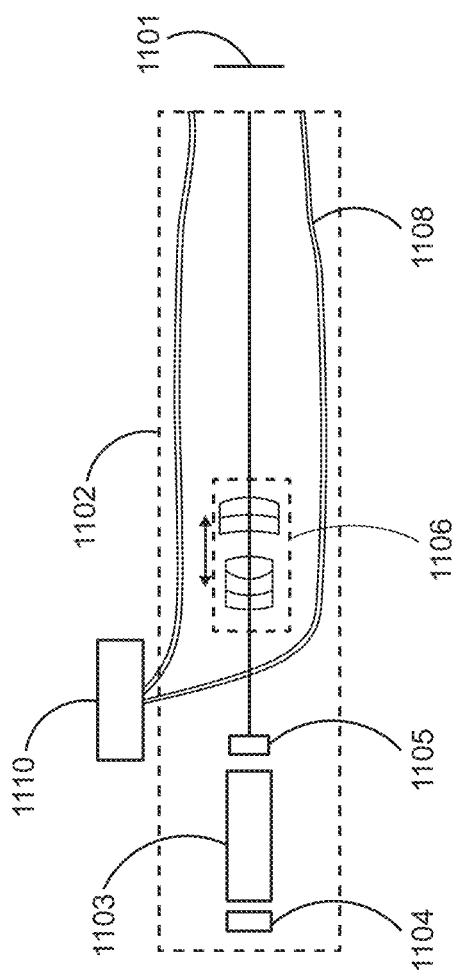
FIG. 3 illustrates a handpiece with both illumination and imaging optical elements inside the handpiece according to one embodiment of the present invention.
Figure 4:
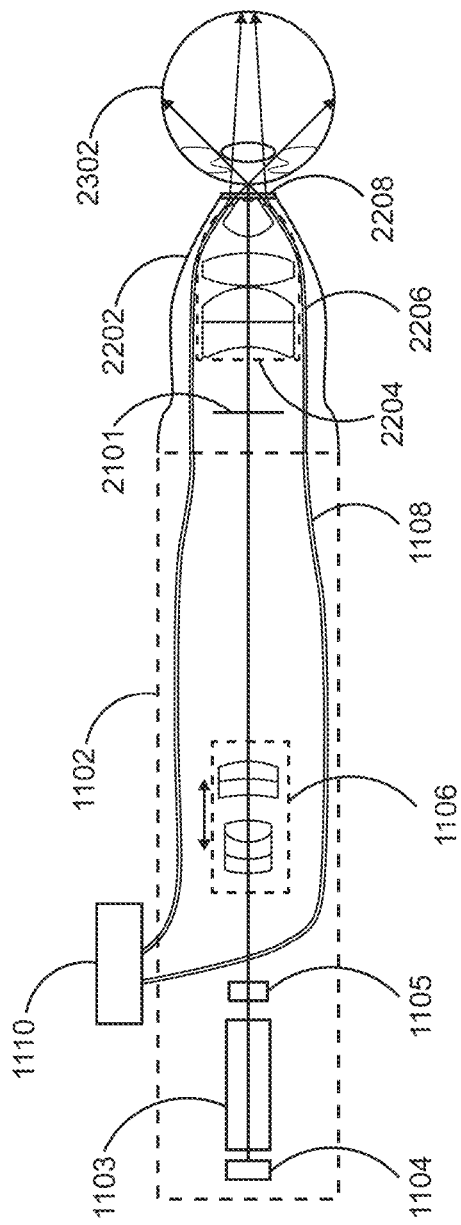
FIG. 4 depicts a patient eye positioned next to a lenspiece that is in mechanical connection with a handpiece, with the imaging optical elements and the illumination path inside both the handpiece and the lenspiece according to one embodiment of the present invention.

Referring to FIG. 3, the dashed rectangular box represents a handpiece 1102. Inside the handpiece 1102 is a visible wavelength image sensor 1104 which can be a three-chip or a one chip image sensor connected to a live video display (not shown), a color splitting prism (in the case of a three chip image sensor) or an optical path length compensation block (in the case of a one chip image sensor) 1103, a deep red and/or near infrared cut filter 1105, and an axially movable lens combination 1106. The lens combination 1106 focuses and relays a real image from somewhere at or near the intermediate image plane 1101 to the image sensor 1104. The lens combination 1106 may comprise a front-position doublet and a rear-position triplet. Inside the handpiece, there is also an illumination light path comprising a number of fibers 1108 (which can be the same fiber as the fiber in the lenspiece), that can be bundled to one or more light emitting port(s) and terminate at the front end of the handpiece. Notably as shown in FIG. 4, in some embodiments, the imaging relay from the retina of a patient eye 2302 to the intermediate image plane 1101 as shown in FIGS. 3 and 2101 as shown in FIG. 4 is accomplished by the lenspiece 2202, and from there the image is relayed and focused to the image sensor 1104. As discussed, fibers 1002 (as shown in FIGS. 2B and 2C) or 2206 (as shown in FIG. 4) or 1108 (as shown in FIGS. 2C, 3 and 4) may include the use of plastic fibers with high numerical aperture (NA). In some embodiments, the other ends of the fibers 1108 (also referred to herein as "illuminator fibers") can be bundled together and optically connected to a light source(s) 1110 which can reside inside or outside the handpiece 1102. The light source(s) 1110 can be a white light source or a red, green and blue light source. The light source(s) can be operated in flashing mode in synchronization with the operation of the image sensor 1104 to reduce and minimize unnecessary exposure of illumination light to a patient eye. The sequential flashing of the red, green and blue light source(s) or the white light source can be electronically controlled to emit either a single-color wavelength or more than one color wavelengths. The fibers 1108 are configured to collect and couple the illumination light from the light source(s) and transmit the illumination light along the illumination path in the handpiece.

In one embodiment, the use of fibers with high numerical aperture (NA) are contemplated. An example is the TORAY RAYTELA PQE series plastic fibers that have a numerical aperture (NA) of 0.64. Said fibers ultimately provide illumination light to the lenspiece and then from a skewed circular array of fiber ends at the end of the lenspiece to span a wide enough range to cover the desired angular field of view on the retina of a patient eye.

Referring to FIG. 4, the handpiece can be combined with any lenspiece of a certain angular field of view coverage designed to be used with the presently disclosed system as long as the lenspiece can form a real or virtual intermediate image at or near the intermediate image plane 1101 or 2101 in front of the handpiece. In addition, in one embodiment the lenspiece and handpiece achieve a wide angular field of view ("FOV") of up to 130 degrees relative to the center of the eye globe. As illustrated in FIG. 4, a 130-degree FOV lenspiece is shown attached to the handpiece as an example. On the right side of the handpiece, a cone-shaped housing 2202 represents the body of a 130-degree FOV lenspiece. Inside the lenspiece, there is a lens combination 2204 defining an imaging path and its associated optical axis, an illumination light path 2206 comprising a number of fibers optically coupled with those fibers 1108 in the handpiece. The front optical element 2208 can function both as a front contact lens of the lens combination 2204 for forming an intermediate image of an object at or near the intermediate image plane 2101, and also as a transmission window for the illumination light to pass through, as well as an optical sealing window. In some embodiments, the handpiece and lenspiece comprise an angular FOV of at least 110 degrees relative to the center of the eye globe. In other embodiments, the handpiece and lenspiece comprise an angular FOV of at least 120 degrees relative to the center of the eye globe.

Continuing with FIG. 4, a human eye 2302 is shown at the far right, with the lenspiece positioned next to the cornea and a light coupling medium (gel) filling the gap between the front contact lens 2208 and the human eye 2302. At this position, the illumination light beams coming from the ends of the optical illuminator fibers 2206 enter the eye with a skewed beam direction or angle and a flattened angular light intensity distribution, as well as a cone angle (or numerical aperture) large enough to illuminate the desired area on the retina of the eye 2302. The circular array of illuminator fiber ends are arranged such that the light output pointing lines, being a central line of a fiber end's light emitting cone, are not on a meridional plane containing the optical axis of the imaging path but are at a skewed angle relative to the optical axis.

In some embodiments, variation in angle of the lenspiece relative to the eye allows various views for optical examination. Notably, with a certain coupling gel gap distance the illumination light rays will pass through the cornea outside the imaging path but can still enter the eye without being blocked by the iris of the human eye 2302. Standard gel gap tolerance ranges apply with respect to the cornea and the front contact lens 2208. For example, the gel gap distance can be from 0.5 mm to 1.0 mm. In some embodiments, the illumination uniformity variation as detected on the image sensor is less than 25% or even less than 10%. This illumination variation is greatly reduced relative to conventional systems, which typically result in at least fifty percent variation resulting from generally a donut shaped illumination annular ring on the retina.

Figure 5:
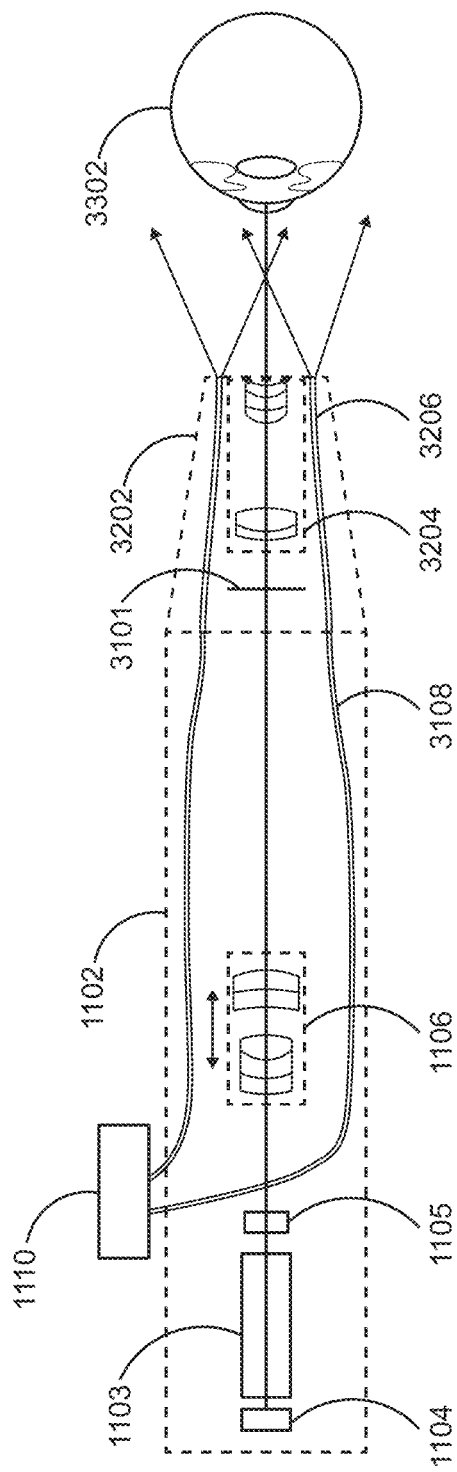
FIG. 5 depicts a patient eye positioned at a distance from a portrait lenspiece that is in mechanical connection with a handpiece, with the imaging optical elements and the illumination path inside both the handpiece and the portrait lenspiece according to one embodiment of the present invention.

Referring now to FIG. 5, there is shown the case of a portrait lenspiece 3202 attached to the handpiece 1102. Inside the portrait lenspiece is a lens combination 3204 that can form an intermediate real image of the object (an external image of a patient eye as shown in FIG. 5) at or near the intermediate image plane 3101. There is also an illumination light path 3206 comprising a number of fibers or fiber bundles that relay the illumination light from the handpiece to the portrait lenspiece and exit the portrait lenspiece to flood illuminate an object. In this case, there is a relatively large air gap between the portrait lenspiece 3202 and the patient eye 3302, and no coupling gel is used. The illumination light from the optical illuminator fibers 3206 can be bundled into four light emitting ports and spread to illuminate the external of the patient eye 3302. Depending on the air gap distance, a larger or smaller external feature of the patient eye or the patient face may be illuminated and digitally imaged. External background lighting like that from room lighting can contribute part of the illumination.

Figure 7A:
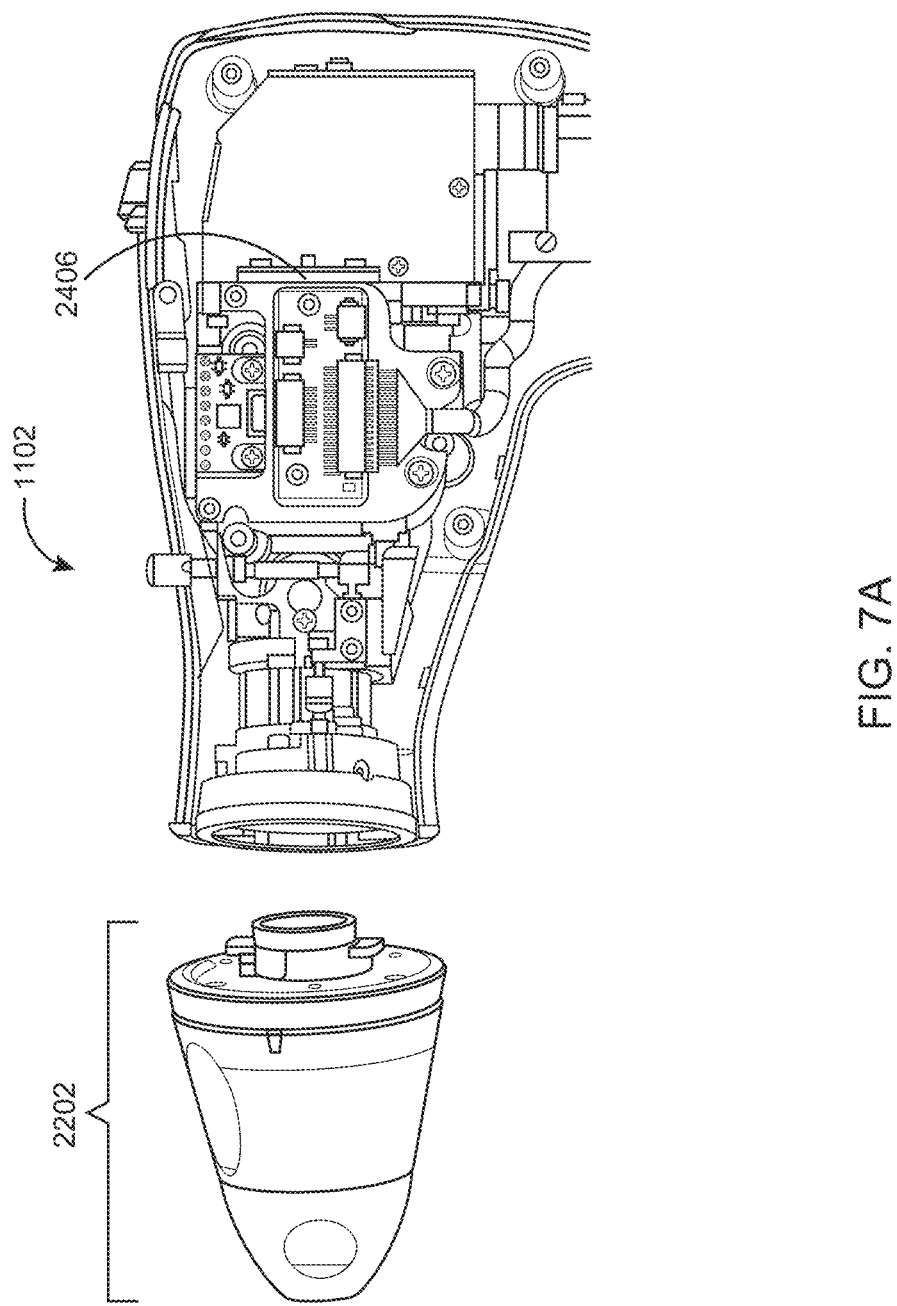
FIG. 7A depicts a lenspiece just separated from a handpiece, including a detailed exterior view of the lenspiece in addition to a detailed view of the handpiece core.
Figure 7B:
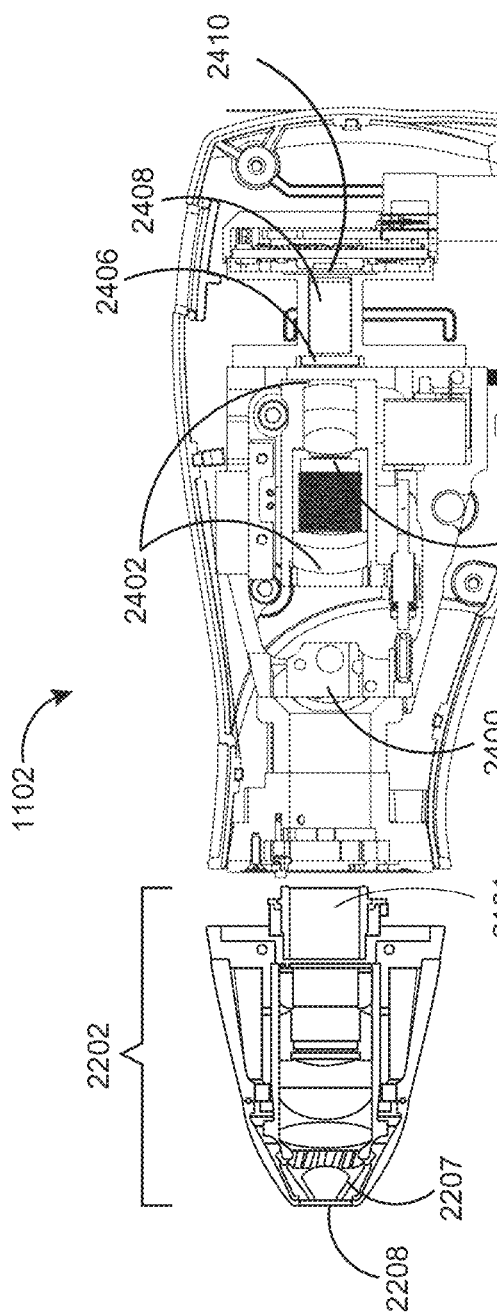
FIG. 7B depicts a lenspiece just separated from a handpiece, including a detailed view of the contact lens, cone shaped lens, intermediate image plane, FA filter/optic window, focus group, aperture stop, IR/far-infrared block filter, color splitting prism spacer block or an optical path length compensation block, and image sensor(s) according to one embodiment of the present invention.
Figure 7C:
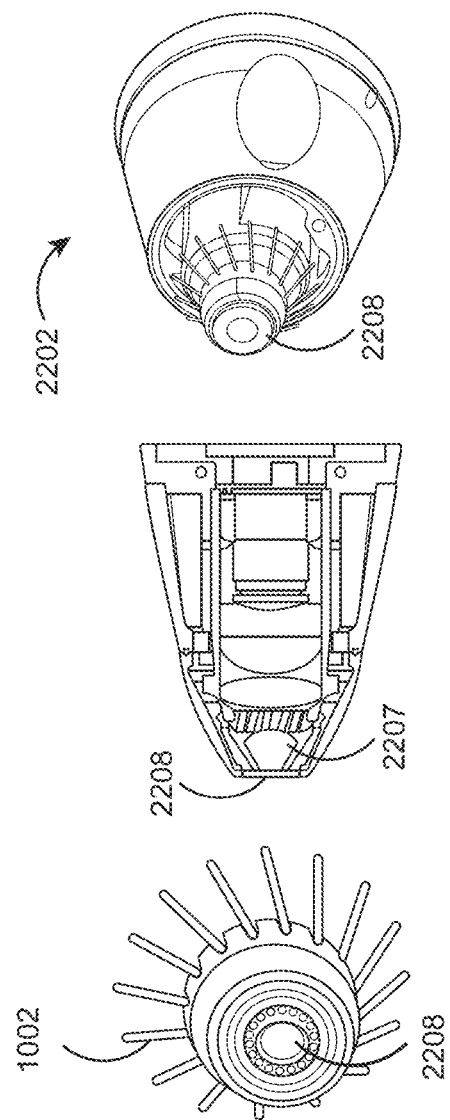
FIG. 7C depicts a lenspiece interior and lenspiece exterior, depicting the skewed fiber array next to the contact lens inside the lenspiece according to one embodiment of the present invention.

In some embodiments, as shown in FIGS. 7A-C, the lenspiece 2202 and handpiece 1102 include detailed exterior and interior core elements essential to the functioning of the eye imaging apparatus. For example as shown in FIG. 7C as core elements of the lenspiece 2202, illumination fibers 1002 are arranged in a circular array manner on the side of the conic lens 2207 behind the contact lens 2208 with the lenspiece fiber ends pointing at a skewed angle with respect to the optical imaging path axis. Also as shown in FIG. 7B, the lenspiece 2202 and handpiece 1102 include a contact lens 2208, a cone shaped lens 2207, an intermediate image plane 2101, an optic window or a green band pass filter 2400, a focus group 2402, an aperture stop 2404, an IR or far red block filter 2406, optical path length compensation block or color splitting prism 2408, and a three chip or one chip image sensor 2410. What is not shown in FIGS. 7A and 7B is the electronic communication between the image sensor 2410 (which can be one-chip or three chip) and the illumination light source(s), which synchronizes the flashing of the illumination light source(s) with the electronic shutter's opening and closing of the image sensor. It should be noted that in eye interior imaging, light safety requires that the total amount of light sent to a patient eye be controlled to a safe limit. If the illumination is continuous, then when the electronic shutter of the image sensor is closed, the illumination light shining onto the interior of the patient eye during this period is wasted which reduces the illumination usage efficiency and in addition, in terms of light safety, it also contributes additional unnecessary risk. This is especially the case when a one-chip color image sensor is used, as more illumination light is needed because some of the illumination light will be inherently rejected by the arrayed color filters as will be discussed shortly. In this respect, as an embodiment of the present invention, high frequency response illumination light source(s) of red, green, blue and/or white colors, such as those made from different color band LED dies with or without a yellow phosphor coating, is(are) used in combination with the image sensor not only to improve illumination usage efficiency (i.e. to reduce and minimize unnecessary exposure of the illumination light to a patient eye) but also to potentially reduce color cross talk and hence improve color fidelity as will be discussed below.

Figure 8A:
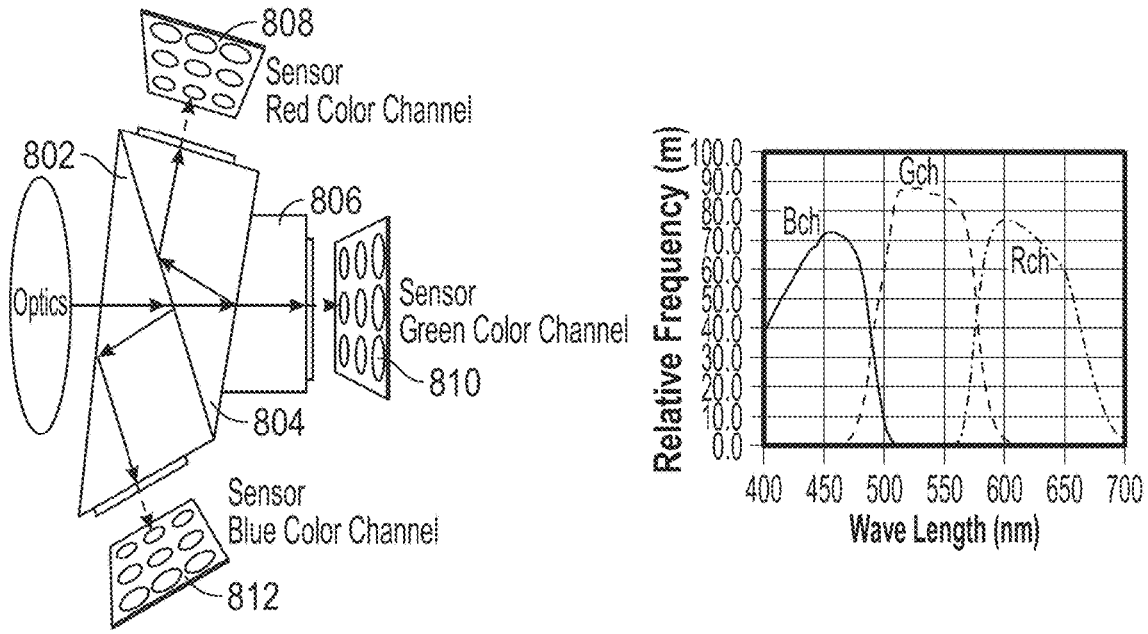
FIG. 8A depicts a three-chip image sensor and its corresponding spectral curves of the red, green and blue wavelengths according to embodiments of the present invention.
Figure 8B:
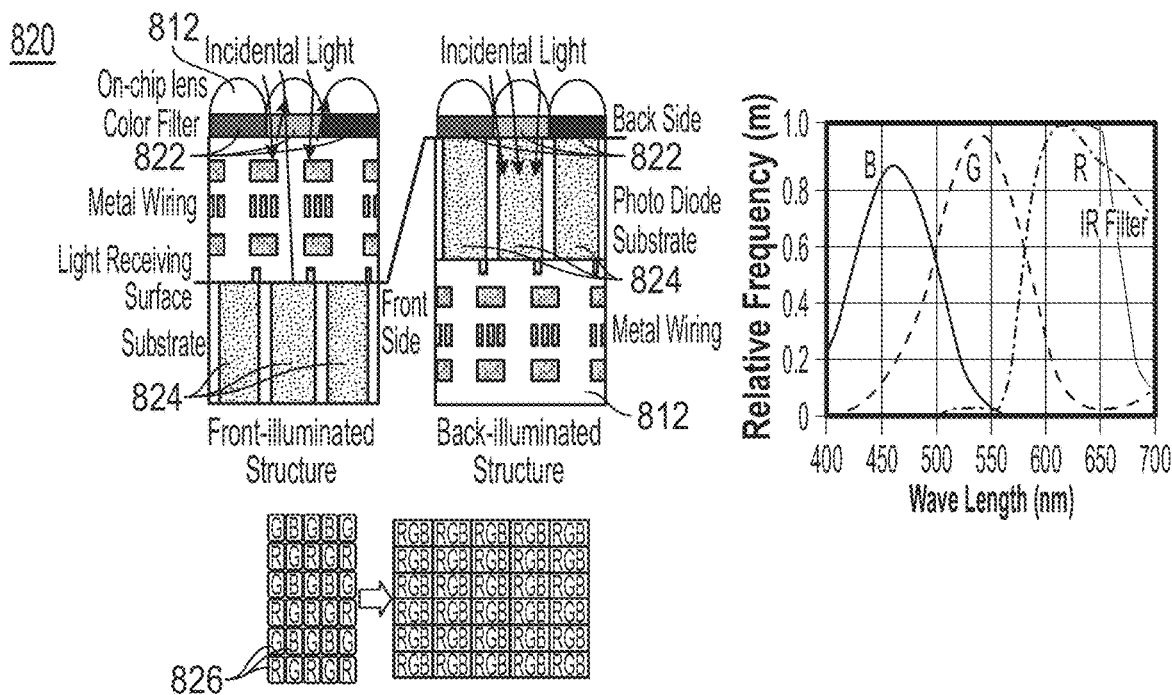
FIG. 8B depicts a one-chip color image sensor and its corresponding spectral curves of the red, green and blue wavelengths according to embodiments of the present invention.

FIGS. 8A and 8B show the difference between a three-chip image sensor comprising a discrete red color sensor 808, a discrete green color sensor 810, and a discrete blue color sensor 812 (FIG. 8A) and a one-chip image sensor 820 (FIG. 8B) in terms of how the red, green and blue channel images are obtained and the difference in the corresponding spectral response curves of the different color channels. The color splitting in the three-chip image sensor is achieved with three bulk dielectric coating based color splitting filters at the interfaces of the three optical medium blocks of 802, 804, 806. Hence, the color splitting in terms of the steepness of the color cutoff edges is generally substantially better than that of the one-chip image sensor. In the one-chip image sensor embodiment, arrayed color filters 822 are patterned on top of different photodetectors 824 that are positioned to define a pixel array comprising a plurality of pixels 826 and hence cannot be made to have the steep color cutoff edges as in the bulk dielectric coating case. Therefore, in conventional use, a one-chip image sensor when used with a continuous broad white illumination light source will thus result in more color mixing or cross talk. In addition, the patterned color filters will reject certain color bands instead of fully utilizing all the incoming photons and as a result, some illumination light will be wasted. Although the electronic gain of a one-chip image sensor can be increased to compensate for the rejected illumination light, the increased electronic gain will result in more electronic noise and cause the pixels 826 to saturate more easily as the illumination light is increased, resulting in saturated hot pixels regions on the final image. However, the cost of a one-chip image sensor is much lower than that of a three-chip image sensor. Therefore, in terms of cost saving, if the amount of illumination light can be controlled to within the light safety limit and those issues associated with illumination usage waste, background electronic noise, more easily reached saturation, and color cross talk can be controlled to be acceptable, a one-chip image sensor can still be considered as an option.

An embodiment of the present invention is to combine a one-chip image sensor with synchronized flashing of red, green and blue or white illumination light to improve illumination usage efficiency and also possibly color fidelity. The sequential flashing of the red, green and blue or white illumination light is synchronized with the electronic global shutter of the one-chip image sensor, thus reducing/removing the amount of wasted illumination light during the shutter-closed period. In addition, color mixings or cross talk can also be potentially reduced via the use of a triband filter to suppress the spectral components in the color crossing-over region for the case of a white light source or the use of better separated (i.e. not overlapping) spectral bandwidth of red, green and blue light sources for the tri-color light source case. In some embodiments of the invention, color images are created using an RGB illumination light source that contains a red color wavelength, a green color wavelength and a blue color wavelength. Said light source may also include a broadband wavelength "white" LED light beam that is created by blue LED dies covered with a yellow phosphor coating.

Figure 9A:
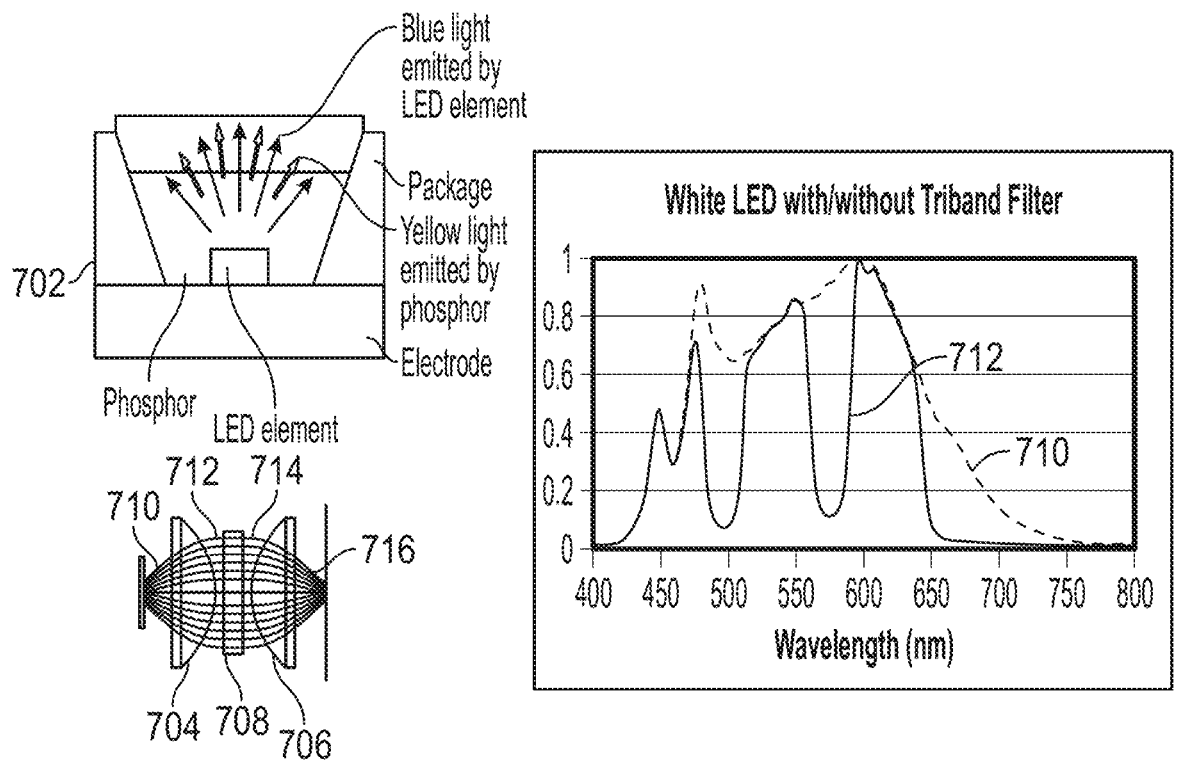
FIG. 9A depicts two paired condensing lenses and a tricolor or triband filter in between the two condensing lenses to clean up the spectrum of the light source and produce better defined red, green and blue color wavelengths according to embodiments of the present invention.
Figure 9B:
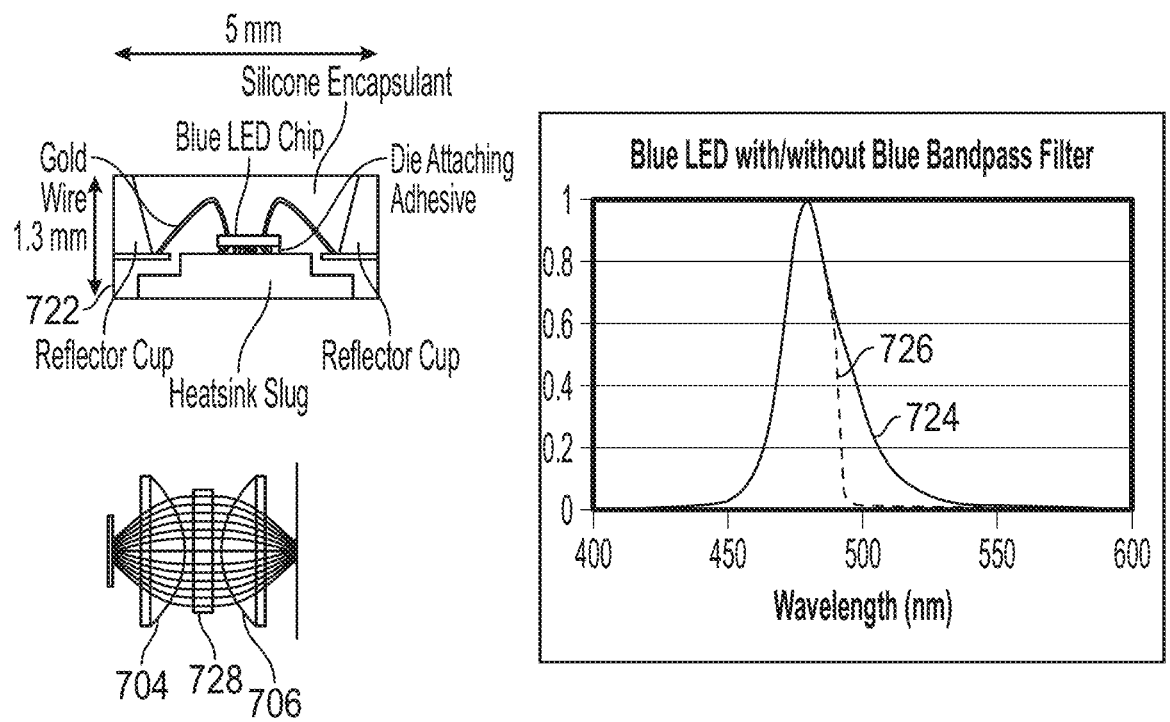
FIG. 9B depicts a blue LED die, two paired condensing lenses and a blue wavelength pass filter in between the two condensing lenses to remove the green tail of the blue spectrum of the light source, and the spectral curves before and after the spectral cleaning according to embodiments of the present invention.

Notably, a photodetector die may be used to facilitate monitoring of light output in real time. Benefit of having a light detection die is that when each color (R, G, B or White) is flashed, the amount of each color light emitted from the light source can be monitored in real time. In some embodiments, a calibration can be done before hand to establish a response curve to correlate the illumination detector signal to the amount of each color light emitted from the light source. Referring now to FIGS. 9A and 9B, a white LED die 702 and a blue LED die 722 are shown respectively. The combinations of the blue LED dies and yellow phosphors generate "white" light. In one embodiment, the "white" light source comprises multiple LED chips/dies of different blue peak wavelength with different yellow phosphors that are combined/mixed to make the "white" illumination light spectrally broad.

In one embodiment, the light from each LED chip/die is coupled through a lens-based coupling mechanism into a multiple number of small diameter glass fibers. These fibers are then bundled together with random arrangements. As a result, at the end of the fiber bundle light output end, the overall spectrum of the light output is mixed and randomized to cover a desired overall spectral range. In some embodiments, the proximal LED lighting module includes a plurality of LEDs. The plurality of LEDs may be of extra brightness, surface oriented, or bright white LEDs.

In some embodiments, illumination filters facilitate improved performance, said illumination filters comprising tricolor or triband filters 708, blue wavelength pass filters 728, and the like. In some embodiments, two condensing lenses 704 and 706 are combined with a tricolor or triband filter 708. Said tricolor or triband filter permits one to spectrally remove unnecessary spectral components from irradiating the eye and reaching the image sensor, including the UV and NIR wavelengths as well as wavelengths in between two neighboring color channels. The spectral filtering or "cleaning" is achieved with a first condensing lens 704 arranged to optically collimate the divergent light beam 710 emitted from the end of the fiber bundle into a collimated beam path 712. The tricolor/triband filter 708 may be positioned in the collimated beam 712 path to only pass light in desired blue, green and red color wavelength bands, defining a filtered collimated beam 714. A second condensing lens 706 is positioned in the filtered collimated beam 714 path optically downstream of the tricolor or triband filter 708 to convert the collimated beam 714 to a converging beam 716 to refocus the filtered collimated beam 714 to a relatively small light spot. An optical fiber cable (not shown) comprising multiple plastic fibers (each plastic fiber can have a relatively large fiber diameter of 0.75 mm) can be inserted in position to collect the illumination light from the spectrally cleaned light source(s).

As shown in FIG. 9A, the spectral graphs 710 and 712 respectively show the normalized spectral curves of the white LED light output measured before and after the insertion of the tricolor or triband filter 708. The spectral cleaning suppressed spectral features in the ultra-violet and near infrared. Removal of the ultra-violet spectral component is critical as such light component is significantly more hazardous to a patient's eye than the visible spectral component. Removal of the far red or near infrared is critical as well because these far red and near infrared spectral components can be captured by the red color channel of the image sensor, regardless of whether it is a one-chip or a three-chip image sensor, and cause the red channel image to be more blurred than desired simply because the far-red and near infrared best focused image will be further away from well-focused image plane of the green channel image.

In some embodiments, as shown in FIG. 9B, a blue band pass filter also suppresses spectral features after "spectral cleaning" in the ultra-violet and green and red region so the blue FA (fluorescein angiography) excitation light is spectrally purer. The spectral graphs 724 and 726 respectively show the normalized spectral curves of the "blue" LED light output measured before and after the insertion of a blue wavelength band pass filter 728 in between the two condenser lenses 704 and 706. It can be seen that the spectral tail that penetrates into the green channel has been substantially suppressed by the blue wavelength band pass filter. In the case of fluorescence angiography imaging, a green wavelength band pass filter or a long pass filter that removes blue light may be disposed within the imaging path of the handpiece.

Figure 10:
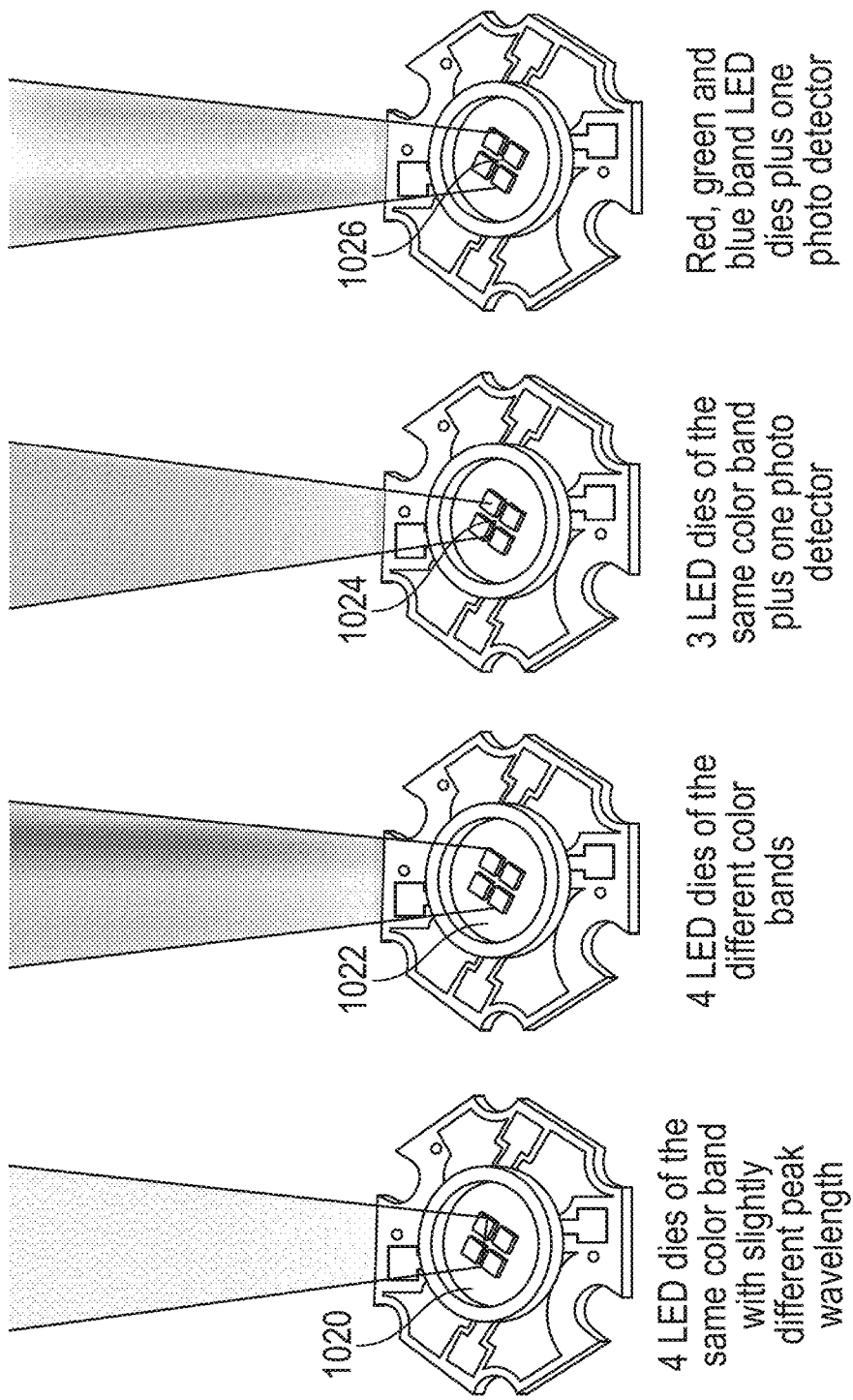
FIG. 10 depicts different approaches of arranging multiple LED dies with or without photodetector die(s) on the same substrate of the Excelitas ACULED® DYO™ family light source according to embodiments of the present invention.

In some embodiments, multiple LED dies are arranged on the same substrate such as the Excelitas ACULED® DYO™ family light source as shown in FIG. 10. In such an embodiment 1020, multiple LED dies of the same color band but with slightly different peak wavelength can be mounted on the same substrate. In one embodiment, the color wavelength is the blue color wavelength and the light source is used for fluorescence angiography retina imaging. In another embodiment 1022, the multiple LED dies are of the red, green and blue color wavelengths bands. In still another embodiment 1024, each color wavelength band can comprise a number of LED dies of the same color wavelength band but with slightly different peak wavelength so the overall color band can be broadened to desired spectral width. Such a light source can be used for color imaging in combination with a three-chip or one-chip image sensor. In some embodiments 1026, one or more photo detectors can be mounted on the same substrate as the LED dies to monitor the amount of light emitted from the same substrate. In both the blue and the white or RGB light source embodiments, a blue wavelength band pass filter or a tricolor or triband filter can still be used to filter the spectrum as shown in FIGS. 9A and 9B.

Given the fact that each color LED die generally has only a limited FWHM (full width at half maximum) spectral wavelength width of about 40 nm and a broader spectral wavelength for each R, G, B color is generally more preferred. In one embodiment, an Excelitas' ACULED® DYO™ configuration of LED dies is employed. In such an embodiment, each red, green, and blue color elements can comprise multiple LED dies with a somewhat separated center wavelength and overlapping spectrum to enable a relative full coverage of each color band spectrum. In some such an embodiment, the LED dies within each color wavelength band can be simultaneously flashed. Similar to the Excelitas' ACULED® DYO™ family, each LED color band can be individually electrically activated to enable sequential pulsing and/or flashing of various wavelengths. Furthermore, more than one LED die can be combined for each visual wavelength band and pulsed simultaneously at a much higher frequency (at least 10 times and preferably more than 100 times the frame rate of the image sensor) to enable pulse width modulation (PWM) based light intensity control. In other words, flashing of either one color channel or the whole white channel comprises flashes that are synchronized with the electronic shutter opening and closing of the image sensor and at the same time, within each flash the illumination light output is pulsed at a frequency at least 10 time and preferably more than 100 times the frame rate of the image sensor with the duty cycle or the pulse peak value of the high frequency pulse being changed depending on the desired amount of effective illumination light of that color band.

In some embodiments, when a one-chip image sensor is used in the handpiece, the light source may comprise an RGB light source with each color wavelength band synchronized sequentially with the electronic shutter of the one-chip image sensor. One advantage of the Excelitas' ACULED® DYO™ configuration as shown in FIG. 10 is the compact die size and each die in the configuration is independently electronically addressable so that fast synchronized PWM pulsing in combination with sequential cycling-based flashing of the red, green and blue color band can be realized. In terms of light coupling, to distribute all colors evenly into a fiber bundle, a light homogenizer (including a CPR (compound parabolic reflector), a diffuser and a light pipe) can be arranged between an ACULED® DYO™ and the end of a fiber bundle. To improve light coupling efficiency, other lens(es) and/or reflector(s) can be used to further match the overall area and the numerical aperture or light acceptance cone angle of the fiber bundle.

As discussed, each color wavelength LED die generally has only a limited FWHM (full width at half maximum) spectral wavelength width of about 40 nm while a broader spectral wavelength for each R, G, B color may be advantageous in come embodiments, although such embodiments do not limit the scope of the invention. In one embodiment, the Excelitas' ACULED® DYO™ configuration of 4, 6, or 9 LED dies may be employed, although configurations of any number of dies are contemplated and included within the scope of the invention. In such embodiments, each R, G, B color wavelength band may comprise two or more LED dies with separated center wavelengths and overlapping spectra to enable a relatively full coverage of each color wavelength band. In such a case, the two or three or more LED dies within each color wavelength band can be simultaneously flashed with or without PWM to create a broader wavelength single color light emission spectrum.

Notably, in some embodiments the one-chip image sensor has its own Bayer Pattern color filter array, which can further reject light not belonging to the expected color channel. Accordingly, when the red color LED dies are flashed, only the red channel image from the one-chip image sensor will be saved as the red channel image. Similarly, when the green color LED dies are flashed, only the green channel image from the one-chip image sensor will be saved as the green channel image, and when the blue color LED dies are flashed, only the blue channel image from the one-chip image sensor will be saved as the blue channel image. These red, green and blue color images are then digitally registered and combined to produce a full color image. In addition, to further control color cross talk or mixing, in another embodiment, bulk dielectric steep cutoff edge color filters may be arranged on top of the corresponding single-color wavelength LED dies to remove the tail part of the emitted single color wavelength spectrum.

Figure 11A:
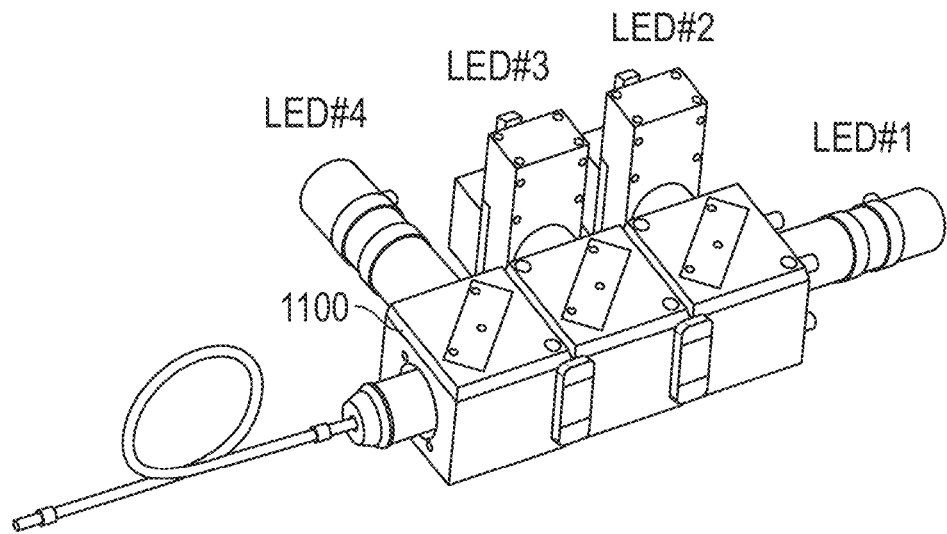
FIG. 11A depicts a multi-wavelength source with 4 LEDs of different visual wavelengths being combined and launched into a fiber bundle per the Mightex™ multi-wavelength LED source design according to embodiments of the present invention.
Figure 11B:
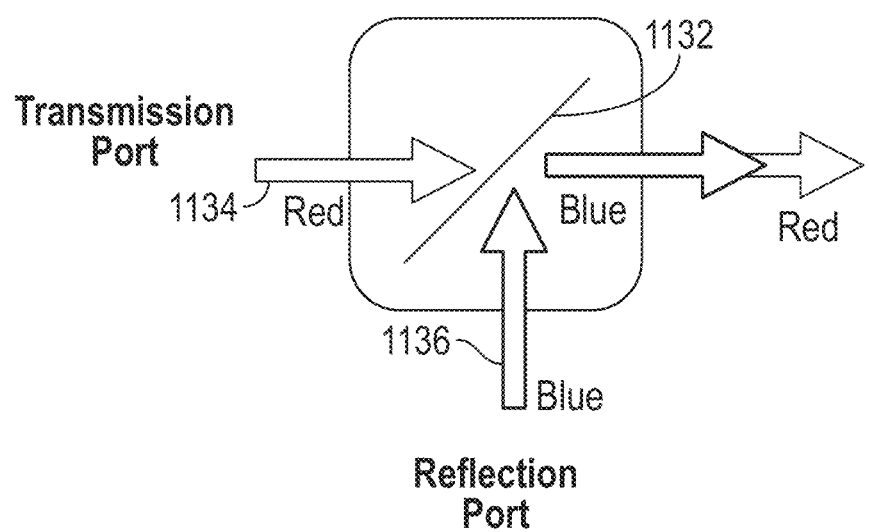
FIG. 11B depicts the use of a multi-wavelength beam combiner to combine two LED collimators of different wavelengths into a single collimated beam per the Mightex™ multi-wavelength LED source design according to embodiments of the present invention.

As described above, the presently disclosed method and system described herein contemplates a multi-wavelength or heterogeneous illumination source 1100. As depicted in FIGS. 11A-11B, said multi-wavelength illumination sources 1100 may comprise multi-wavelength LED sources, for example, the Mightex™ multi-wavelength LED sources as discussed herein and/or comparable sources known in the industry. Notably, "multi-wavelength" light and "heterogeneous" light are used interchangeably herein. In some embodiments, multi-wavelength sources are operably attached to beam mixers 1132 to combine two LED collimators of different wavelengths 1134, 1136 (combined for example, through a transmission port and/or a reflection port) into a single collimated beam as shown in FIG. 11B.

In some embodiments, multiple combiners may be cascaded to combine more than two LED collimator sources. In some embodiments, the beam combiner is a high-performance dichroic beam splitter that combines two wavelengths with >95% efficiency. As shown in FIG. 11A, a multi-wavelength source 1100 with 4 LEDs of different colors may be combined and launched into a fiber bundle. Similar to the Excelitas' ACULED® DYO™ family, each LED may be individually electrically addressed to enable synchronized sequential flashing of different color wavelengths with or without PWM. Furthermore, more than one LED die may be combined for each color wavelength band and flashed simultaneously with or without PWM to increase the single color spectral color width as discussed in the previous case. In the above embodiments, the beam from each LED is already collimated before being combined. Further, the combination may ensure a relatively favorable beam spatial overlap. Finally, the above embodiments have no absolute need for a homogenizer although such an optical element can be used to further improve the homogenization of the combined beam.

In one embodiment of the one-chip image sensor, as shown in FIG. 8B, a back illumination-chipped, high quantum efficiency, high frame rate, global shutter image sensor with a Bayer Pattern color filter array is employed. The preference for a back-illumination chip is that it generally has a better quantum efficiency than a front illumination image sensor. However, a front-illuminated chip is contemplated and included within the scope of the invention and may be used in some embodiments of the invention. A frame rate of at least 60 fps, and in some embodiments 90 fps or more, is preferred because with R, G, B flashing in sequential cycling operation, every three flashes will generate a full color frame image and to enable video recording and replay in real time with no apparent lagging, generally a minimum 20 frames per second (fps) video is required. Therefore, with a 60 fps image sensor, one may achieve a 20 fps full color video. With a 90 fps image sensor, one may achieve 30 fps full color video.

An advantage of the present invention relates to the versatility of the design, a design permitting implementation of various electronically-controlled features, adaptive collimators, filters, and the like. For example, in some embodiments, an electronic shutter, such as a global shutter image sensor, is adaptable to operably attach to the illumination and imaging apparatus. Advantageously, with each flash the image sensor's electronic shutter can be synchronized to ensure that all pixels are opened just before the flash is activated and closed right after the flash is deactivated. The flash can be in red, or green or blue or white color or a combination of two or more colors. In one embodiment, the present invention contemplates that the shutter may open and close in an automated fashion, just before and after each flashing respectively.

In terms of controlling the illumination light strength, one embodiment is to directly control the current that drives each LED die with the flashing frequency matching the frame rate of the image sensor. As the current value can slightly influence the spectrum of the LED die light output, which is not desirable, another embodiment is to use the pulse width modulation (PWM) scheme well-known to those skilled in the art to control the effective time-averaged light output from each LED die through the control of the duty cycle. In such a case, the pulse width modulation frequency is much higher (at least 10 times and preferably 100 times or more) than the image sensor frame rate. The flashing of each LED die will effectively comprise a burst of high frequency pulses and the duty cycle of the pulse will change depending on the needed time-averaged amount of light output.

In one embodiment, the PWM duty cycles of the red, or green or blue light sources can be controlled to be different from each other. In another embodiment, the peak current of the PWM pulses for each of the red, green and blue channels can be controlled to be different from each other. In still another embodiment, a combination of the PWM duty cycle and pulse peak current of the red, or green or blue light sources can be controlled to be different from each other. In such a way, the effective optical energy or effective number of photons in each of the red, green and blue color channels from the image sensor can be better white balanced so the resultant electronic gain of the red, green and blue channels are approximately the same after white balancing. To put it in other words, the ratio of multiplication of the PWM duty cycle and/or the pulse peak current and/or a combination of the two from the red, green and blue light sources per the PWM modulation scheme can be maintained relatively constant to control the white balancing operation, and as a result, the final electronic gains of the image sensor's red, green and blue channels is maintained close to the same. This will avoid the situation when at least one of color channel requires a relatively much larger electronic gain (either analog or digital) with respect to the other one or two channels, which can then result in much larger electronic noise in that particular channel and much easier-to-reach saturation or hot pixel of that channel when the illumination of that channel is increased.

In one embodiment, a broad wavelength tap beam splitter may be added before the spectrally combined beam is sent to a fiber bundle to enable a small percent of light from each color or spectral wavelength to be tapped and monitored with a photodetector. In such a case, similar to the Excelitas' case with a photodetector die, when each color is flashed, the amount of each color light emitted from the corresponding light source can be monitored in real time. A calibration may be performed beforehand to establish a response curve to correlate the detector signal to the amount of each color light emitted from the corresponding light source.

Figure 12:
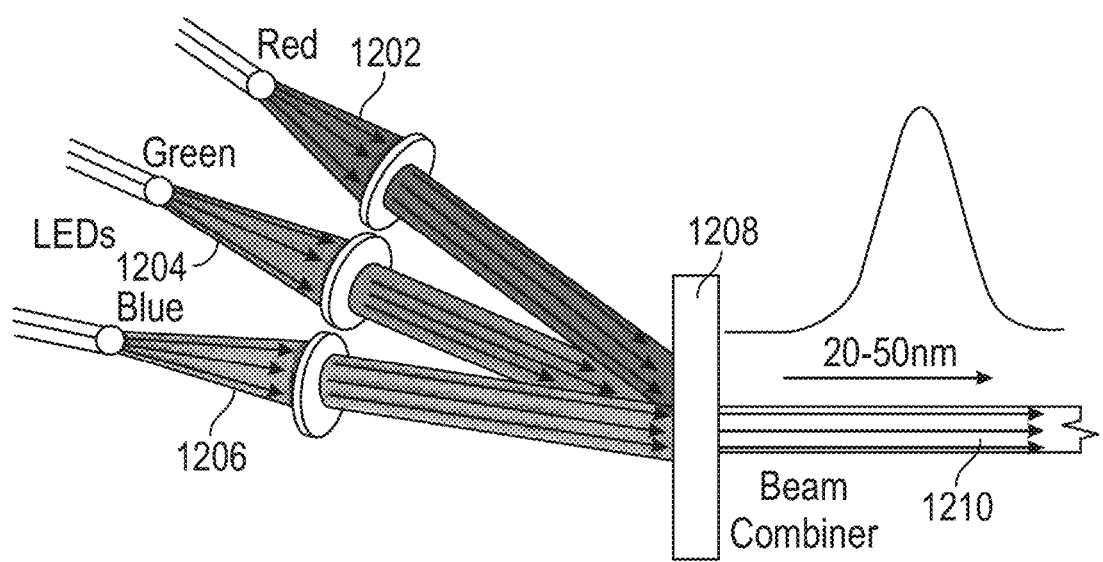
FIG. 12 depicts the use of a diffraction grating combiner being used to combine the red, green and blue light beams into a combined white beam according to embodiments of the present invention.
Figure 13:
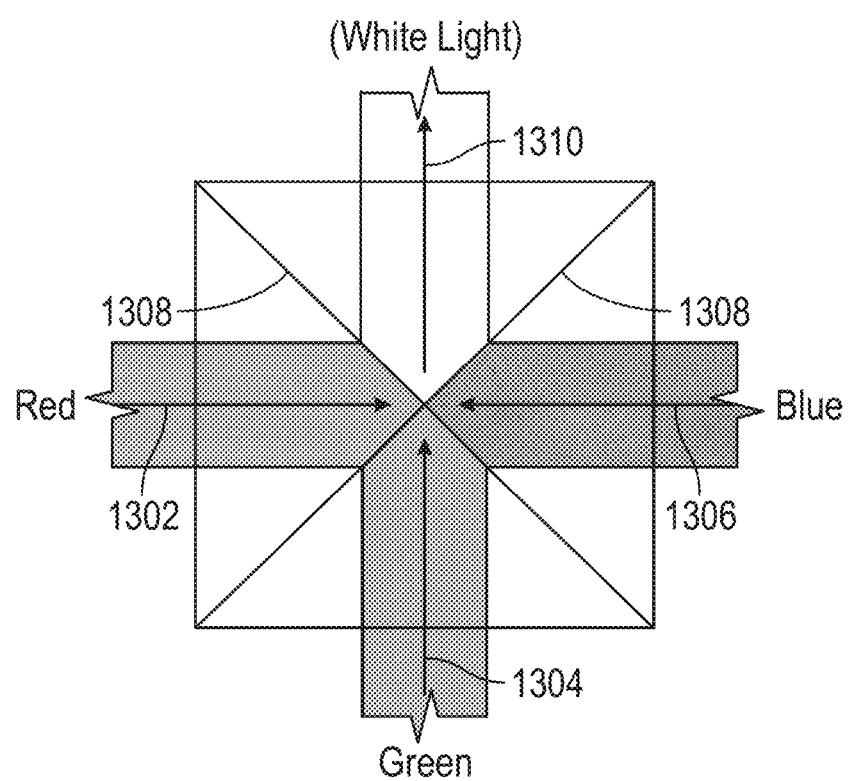
FIG. 13 depicts the use of an X-cube combiner being used to combine the red, green and blue light beams into a combined white beam according to embodiments of the present invention.

In still another embodiment, the synchronized sequentially flashed light source may comprise a diffraction grating combiner, or "diffraction combiner" as shown in FIG. 12. In this case a diffraction combiner 1208 is used to combine the three beams of red 1202, green 1204, and blue 1206 colors into one beam 1210. In yet another embodiment, the red 1302, green 1304, and blue 1306 color wavelengths may be combined into a single beam 1310 using an X-cube combiner 1308 as shown in FIG. 13. The X-cube combiner 1308 may comprise any comparable technology known in the art.

In terms of flashing the red, green and blue color wavelengths, in addition to electrically driving each color wavelength synchronized sequentially, in another embodiment, three shutters can be operated sequentially so that each conducts light during one camera frame duration. As a result, red, green and blue light bursts will be synchronized and sequentially emerge from the combiner. Beside the act of switching, shutters can also be used for controlling the beam power in each of the color channel in order to correctly balance the light power relationship among the three channels. In other words, the herein contemplated invention involves illuminating a location within the eye with light beams comprising a heterogeneous distribution of visual wavelengths. Then, images are formed of the eye location provided by sequential activation of each of the visual wavelengths.

In some embodiments, after mixing, the beam is focused onto an entrance aperture of a fiber group using a short focusing condensing lens. A short focus lens is recommended in order to minimize the illumination beam "eye" location, or "spot-size".

Note that in some embodiments like eye external imaging using the portrait lenspiece, due to the large air gap, room lighting can also function as part of the illumination light. In such a case, with the synchronized sequential color illumination scheme for the light source, only part of the total illumination light will be under synchronized sequential visual wavelength control. However, the Bayer Pattern of the one-chip image sensor or the dielectric color filters of the three-chip image sensor will also play the role of separating the visual wavelengths. As shown in FIG. 8B, the benefit of mixing synchronized sequential color wavelengths for the control of illumination light with a Bayer Pattern one chip image sensor is that the color fidelity of the captured image will still be improved relative to the non-synchronized continuous color illumination scheme. In addition, when the controlled port of the illumination light is turned off such that the only illumination light is from room lighting or background light, the captured image will at least match what the high quality Bayer Pattern one-chip image sensor will produce.

When a large room is involved and a 130 degree lenspiece is attached to a handpiece, the illumination light can be on or off while the imaging device is pointing to some distant objects including entertainment, marketing, and/or tradeshow participants for example. In such a case, the contribution of the controlled illumination light is very small compared to room or background light shining onto the distance objects. The presently disclosed scheme will still be able to produce real time color videos.

One thing that may not be well considered in combining a synchronized sequential color illumination scheme with a one-chip image sensor is the white balancing to ensure high visual wavelength fidelity. Traditionally, white balancing for a one-chip color camera requires a white illumination light source and a grey object. In the presently disclosed invention, since synchronized sequentially flashed illumination for each frame does not produce white frames, in one embodiment of the present invention, white balancing is achieved by simultaneously pulsing all of the different R, G, B visual wavelengths. In another embodiment, white balancing is achieved by synchronized sequentially flashing different illumination visual wavelengths in addition to using software to stack or mix the corresponding color channels in order to produce live videos for auto white balancing.

In still another embodiment, the light output strength of different illumination wavelengths is separately and differentially controlled and as long as the amount of light reaching a patient eye is safe, the gain of the red and blue channel of the image sensor can be tuned to comparable signal strength as the green channel in order to reduce corresponding noise. This would typically result in a more well-defined captured image, particularly when the gain of a particular color channel is required to be set to a relatively high value.

In yet another embodiment, light emission from standard hospital room lighting is used as a reference to achieve auto white balancing and then the light output strength of the synchronized sequentially flashed colors may be tuned to approximately match that of the standard hospital room lighting to recreate the same relative gain of the blue and red frames relative to the green frame. In such a case, color fidelity will not be much different whether the effective illumination is coming from illumination source of the device or from the room lighting.

Notably, the presently disclosed design may be easily adapted to a three-chip image sensor case when the Bayer Pattern one chip image sensor is replaced with a three-chip image sensor if an end user prefers a higher quality sensor at a higher cost. In some embodiments, a scheme is developed to transform synchronized sequential color illumination into mixed white illumination. To further this example, as a benefit, the video frame rate may also be increased. In yet another embodiment, light collection efficiency may be enhanced as signals received by each color channel for every frame are collected and used to produce a full color image in the three-chip image sensor case.

Note that the above-disclosed concept may be easily expanded to enable multi-spectral imaging. In one embodiment, the illumination light source can comprise a relatively large number of narrow wavelength LEDs or even lasers that are spectrally spaced or separated from each other at a desired spectral position as needed to produce the multi-spectral image. Each LED or laser may be flashed synchronized sequentially and if the center wavelength of the LED or laser is within a certain color channel of the one-chip image sensor or the three-chip image sensor, the signal from that corresponding color channel may then be extracted to produce the single spectral image. After all the single spectral images are collected, they can be reproduced to provide the multi-spectral images.

In other embodiments, the one-chip color image sensor is not limited to the Bayer Pattern filter design; other patterned area filter array designs may be used. In addition, the color channels do not need to be restricted to red, green, and blue as other color combinations may also be used, including a near infrared channel which can be very useful for retinal choroid layer imaging. In such a case, a near infrared LED or a number of near infrared LEDs may be used as part of the illumination light source.

In summary, a new device and system has been disclosed. As described herein, the present invention contemplates optical fibers with high numerical aperture (NA), skewed pointing angles, light spatial intensity distribution conversion, and high frequency response light sources operating in flashing illumination mode in synchronization with the electronic shutter of an image sensor. As a result, in addition to the fact that the illumination light can span a wide enough coverage range with desired intensity distribution to cover a desired angular field of view on a retina, unnecessary exposure of illumination light to a patient eye is also reduced and minimized. Furthermore, color images of the interior of the eye may be obtained by illuminating the eye sequentially with either white, or red, green and blue light employing PWM (Pulse Width Modulation) scheme in combination with the flashing of each color. In the case of a one-chip image sensor, this scheme will lead to a reduction in color cross talk. Moreover, the PWM duty cycle and/or pulse peak value of the electronic drive signals for each of the illumination colors can also be controlled for each of the red, green and blue colors to better white balance each color channel of the image sensor. Meanwhile, with the use of a one-chip image sensor, the manufacturing cost of the eye imaging device can be substantially reduced as compared to that of a corresponding three-chip image sensor.

The foregoing description of the present invention has been presented for the purpose of illustration and description. It is not intended to be exhaustive or to limit the invention to the precise form disclosed. Many modifications and variations are possible in light of the above teachings. It is intended that the scope of the present invention not be limited by this detailed description, but by the claims and the equivalents to the claims appended hereto.

What is claimed is:

1. An eye-imaging apparatus comprising:
   a light source selected from the group consisting of red, green, and blue light sources, white light sources, and red, green, blue, and white light sources;
   an image sensor with a shutter having a frame rate, the image sensor being operable to produce a live video signal;
   one or more optical lenses defining an imaging path comprising an optical axis;
   a contact lens; and
   illuminator fibers positioned next to the contact lens;
   wherein the light source is flashed repetitively in synchronization with the operation of the image sensor in producing a live video display for image or video capturing by flashing the light source on when the shutter of the image sensor is opened and the flashing the light source off when the shutter of the image sensor is closed; and
   wherein an averaged amount of light output from each flashing is controlled through pulse width modulation (PWM) having a duty cycle, a pulse peak value, and a pulsing frequency, with the pulsing frequency being at least 10 times the frame rate of the image sensor.

2. The apparatus of claim 1 wherein the illuminator fibers further comprise a prism array-based light profile redistribution element along an illumination light path from the light source to emitting ends of the illumination fibers.

3. The apparatus of claim 1 wherein the light source comprises a white light source.

4. The apparatus of claim 1 wherein the light source comprises red, green and blue light sources.

5. The apparatus of claim 1 wherein the light source comprises red, green, blue, and white light sources.

6. The apparatus of claim 1 wherein the illuminator fibers are positioned such that emitting ends thereof form a circular array disposed and are at a skewed angle relative to the optical axis rather than on a meridional plane containing the optical axis.

7. The apparatus of claim 1 wherein the image sensor is a one-chip color sensor.

8. The apparatus of claim 1 wherein the image sensor is a three-chip color sensor comprising red, green, and blue color sensors.

9. The apparatus of claim 1 wherein the light source comprises red, green and blue light sources with each color channel individually addressable and the flashing is done through a sequentially cycling the flashing of red, green and blue colors.

10. The apparatus of claim 9 wherein the duty cycle of the red, green and blue colors are controlled to white balance the red, green and blue channels of the image sensor.

11. The apparatus of claim 9 wherein the pulse peak value of the red, green and blue bands of the light source are controlled to white balance the red, green and blue channels of the image sensor.

12. The apparatus of claim 9 wherein the duty cycle and the pulse peak value are controlled in combination to white balance red, green and blue channels of the image sensor.

* * * * *